United States Patent
Ma et al.

(10) Patent No.: US 9,505,821 B2
(45) Date of Patent: Nov. 29, 2016

(54) ATAP PEPTIDES, NUCLEIC ACIDS ENCODING THE SAME AND ASSOCIATED METHODS OF USE

(75) Inventors: Jianjie Ma, Belle Mead, NJ (US); Jae-Kyun Ko, Piscataway, NJ (US); Chul-Woo Kim, Seoul (KR); Noah Weisleder, Elizabeth, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 796 days.

(21) Appl. No.: 12/444,288

(22) PCT Filed: Oct. 3, 2007

(86) PCT No.: PCT/US2007/080307
§ 371 (c)(1),
(2), (4) Date: Nov. 19, 2009

(87) PCT Pub. No.: WO2008/060776
PCT Pub. Date: May 22, 2008

(65) Prior Publication Data
US 2010/0222263 A1     Sep. 2, 2010

Related U.S. Application Data

(60) Provisional application No. 60/848,971, filed on Oct. 3, 2006.

(51) Int. Cl.
*A61K 38/00* (2006.01)
*A61K 48/00* (2006.01)
*C07K 14/47* (2006.01)

(52) U.S. Cl.
CPC ........... *C07K 14/4747* (2013.01); *A61K 38/00* (2013.01); *A61K 48/00* (2013.01); *C07K 2319/10* (2013.01); *C07K 2319/21* (2013.01); *C07K 2319/60* (2013.01)

(58) Field of Classification Search
None
See application file for complete search history.

(56) References Cited

U.S. PATENT DOCUMENTS 5,310,663 A * 5/1994 Dobeli et al. ................ 435/69.7
2006/0024700 A1 * 2/2006 Cargill ................ C12Q 1/6883
                                                               435/6.11

FOREIGN PATENT DOCUMENTS

| WO | WO 96/30513 |   | 10/1996 |
|---|---|---|---|
| WO | WO 97/30083 | * | 8/1997 |
| WO | WO 01/81387 |   | 11/2001 |
| WO | WO 01/81387 A1 | * | 11/2001 |
| WO | WO 03/079007 A1 | * | 9/2003 |
| WO | WO 03/102137 A2 | * | 12/2003 |
| WO | WO 2004/110474 |   | 12/2004 |
| WO | WO 2004/110474 A1 | * | 12/2004 |

OTHER PUBLICATIONS

Uniprot Accession No. Q9HBF5 version of Mar. 1, 2001.*
Uniprot accession No. Q9HBF5, Jun. 10, 2008.*
Submitted SNP(ss) details:ss1545746, first entry into dbSNP database Sep. 13, 2000 retrieved on Jun. 19, 2016 at http://www.ncbi.nlm.nih.gov.projects/SNP/snp_ss.cgi?subsnp_id=1545746.*
Reference SNP (refSNP) cluster report: rs7257, Sep. 13, 2000 retrieved Jun. 19, 2016 at www.ncbi.nlm.nih.gov.projects/SNP/snp_ref.cgi?rs=7257.*
International Search Report for PCT/US2007/080307.
Kim et al., Candidate Tumor Suppressor, HCCS-1, is Downregulated in Human Cancers and Induces Apoptosis in Cervical Cancer, Int. J. Cancer, (2002) 97: 780-786.
Ko et al., The Tail-Anchoring Domain of Bfl1 and HCCS1 Targets Mitochondrial Membrane Permeability to Induce Apoptosis, Journal of Cell Sciences, Aug. 2007, vol. 120, No. 16, pp. 2912-2923.
Yang et al., C-Terminal Region of Bfl-1 Induces Cell Death that Accompanies Caspase Activation When Fused with GFP, Journal of Cellular Biochemistry, vol. 94, No. 6, 1234-1247, 2005.
Letai et al. Distinct BH3 domains either sensitize or activate mitochondrial apoptosis, serving as prototype cancer therapeutics. Cancer Cell. Sep. 2002; 2(3): 183-192.
Schimmer et al. The BH3 domain of BAD fused to the Antennapedia peptide induces apoptosis via its alpha helical structure and independent of Bcl-2. Cell Death Differ. Jul. 2001 8(7): 725-733.
Walensky et al. Activation of apoptosis in vivo by a hydrocarbon-stapled BH3 helix. Science. Sep. 3, 2004. 305(5689): 1466-1470.
Kucharczak et al. Constitutive proteasome-mediated turnover of Bfl-1/A1 and its processing in response to TNF receptor activation in FL5.12 pro-B cells convert it into a prodeath factor. Cell Death Differ. Sep. 2005; 12(9): 1225-1239.
Borgese et al. The tale of tail-anchored proteins: coming from the cytosol and looking for a membrane. J Cell Biol. Jun. 23, 2003; 161(6): 1013-1019.
Kaufmann et al. Characterization of the signal that directs Bcl-x(L), but not Bcl-2, to the mitochondrial outer membrane. J Cell Biol. Jan. 6, 2003. 160(1): 53-64.
Johnston et al. Insertion and assembly of human tom7 into the preprotein translocase complex of the outer mitochondrial membrane. J Biol. Chem. Nov. 1, 2002; 277(44): 42197-42204.

* cited by examiner

*Primary Examiner* — Oluwatosin Ogunbiyi
(74) *Attorney, Agent, or Firm* — Bryan D. Zerhusen; Locke Lord LLP

(57) ABSTRACT

Disclosed herein are nucleic acid sequences that encode pro-apoptotic polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of proliferative disorders and bacterial infections using the nucleic acids and proteins of the invention.

12 Claims, 9 Drawing Sheets

ATAP PEPTIDES, NUCLEIC ACIDS ENCODING THE SAME AND ASSOCIATED METHODS OF USE

CROSS-REFERENCE TO RELATED APPLICATIONS

Under 35 U.S.C. §119(e) this application claims the benefit of U.S. Provisional Applications No. 60/848,971 filed 3 Oct. 2006; which is hereby incorporated by reference in its entirety for all purposes.

INCORPORATION BY REFERENCE

In compliance with 37 C.F.R. §1.52(e)(5), the sequence information contained on file name: ATAP_Ma_2007PCT_SEQListv2_ST25.txt; size 32 KB; created on: 14 May 2012 using PatentIn-3.4, and Checker 4.4.0 is hereby incorporated by reference in its entirety. The data in the paper copy of the Sequence Listing, and Computer Readable Form of the Sequence Listing submitted herewith contain no new matter, and are fully supported by the priority application, U.S. Provisional Patent Application No. 60/848,971.

STATEMENT REGARDING FEDERALLY SPONSORED RESEARCH

The U.S. Government has certain rights in this invention pursuant to the following grants: RO1-AG015556, RO1-CA95739, and RO1-HL69000 awarded to Dr. Jianjie Ma by the United States National Institutes of Health (NIH).

FIELD OF THE INVENTION

This invention relates to polypeptides, nucleic acids encoding the same, antibodies that immunospecifically-bind to the polypeptides and associated methods of use.

BACKGROUND

Tail-anchored (TA) proteins, including the Bcl-2 family members, characteristically tether to phospholipid bilayers by a single hydrophobic segment at the carboxy (C)-terminus with the bulk of the molecule located in the cytosol. Bcl-2 is the prototype for a family of mammalian genes and the proteins they produce. The biological function of Bcl-2 related proteins is inextricably linked to their specific subcellular localization; the cytosol, endoplasmic reticitulum (ER) membranes or mitochondria outer membrane (MOM). The Bcl-2 family members have been shown to govern mitochondrial outer membrane permeabilization (MOMP) and can be either pro-apoptotic (e.g., Bax, BAD, Bak, Bok, Bcl-Xs, Bik, Bim, Bid, Egl-1, and Diva among others) or anti-apoptotic (e.g., Bcl-2 proper, Bcl-xL, Mcl-1, CED-9, A1, Bcl-w, and Bfl-1 among others).

Bcl-2 family members have been implicated in a number of disorders, including cancer, for example, melanoma, breast, prostate, and lung; as well as neurological disorders, for example, schizophrenia; and immunological disorders. Cancers and hyperplasias include a variety of very complicated diseases; nevertheless, they all share a common feature that all the cells are hyperproliferative and are able to continue dividing, and do not undergo terminal differentiation. This supports a role for reduced apoptosis in the etiology of these and other related disorders.

While several current cancer therapies promote cancer cell death and inhibit cancer cell growth, many of these therapies are highly toxic to cancer patients and their administration results in a multitude of unpleasant and unbearable side effects. In addition, many of the presently available cancer therapeutics deomonstrate efficacy only against cancers or hyperplasias of specific etiology. Therefore, a treatment that promotes cancer cell death across a broad class of cancer cell types and origins, and is largely non-toxic to patients is highly desirable.

Recently, we demonstrated that anti-apoptotic Bfl-1 contains a unique amphipathic tail-anchoring peptide (ATAP) at amino acids 147-175. As described herein, the Bfl-1 ATAP contains charged amino acids lining to one side of the alpha-helix. Within the human genome, a homologous ATAP sequence is present in another tumor suppressor gene, the human cervical cancer suppressor-1 (HCCS-1). An additional mitochondria-targeting signal (MTS) at the N terminus of HCCS1 contributes to its mitochondria targeting and apoptotic function.

Our experimental results indicate that ATAP peptides are capable of modulating the apoptotic cascade. As such, ATAP peptides can be adapted into a highly effective therapeutic agents to treat a number of diseases, including bacterial infections, cancers and hyperplasias.

SUMMARY

The present invention relates to compositions and methods for inducing apoptosis in a target cell. In particular, the invention relates to the surprising and unexpected discovery that amphipathic tail-anchoring peptides (ATAPs) are potent stimulators of cellular apoptosis, in prokaryotic cells as well as in eukaryotic cells. In eukaryotic cells ATAPs are able to target specifically to mitochondria and induce apoptosis. The apoptotic-inducing activity of the ATAPs indicates that these peptides can be useful as a research and diagnostic tool as well as a therapeutic for treating a variety of diseases and conditions. Moreover, it was also surprising and unexpected that the ATAP peptides of the invention demonstrate strong bactericidal activity. As such, the ATAP nucleic acids and polypeptides of the invention are useful for treating a range of bacterial infections as well. As used herein, "apoptosis" is used to refer generally to cell death, eukaryotic as well as prokaryotic.

In certain aspects, the invention encompasses ATAP nucleic acids, nucleic acid vectors comprising the same, host cells, ATAP antibodies, recombinant ATAP peptides and proteins, pseudopeptides, fusion proteins, chemical compounds, and methods for producing and using the same.

In one aspect the invention relates to compositions comprising ATAP peptides of the general formula (I): bXaXbu-unnunnanXGbnXann$(X)_{1-6}$nn$(X)_{0-2}$b (I). Wherein, n=nonpolar (hydrophobic) amino acids; X=any amino acid; u=polar, uncharged amino acids; b=basic a.a.; a=acidic a.a. In certain embodiments, the invention encompasses nucleic acids that comprise a region that encodes an ATAP of formula I. In additional embodiments, the invention comprises polypeptides that are synthesized from a peptide synthesizer in which the polypeptide comprises an ATAP of formula I.

In certain additional aspects the invention relates to compositions and methods for inducing apoptosis in a target cell. In certain exemplary embodiments, the invention encompasses, for example, the administration, in vivo, in vitro, or ex vivo, of an effective amount of a therapeutic composition of the invention for inducing apoptosis in a cell.

Also described herein are methods for the treatment of a disease or disorder related to cell hyperproliferation, for example, a cancer or hyperplasia; bacterial infections; or immune disorders; comprising administration to a subject in need thereof, a therapeutically effective amount of a nucleic acid encoding an ATAP, or an ATAP itself, together with a pharmaceutically acceptable carrier.

The preceeding general areas of utility are given by way of example only and are not intended to be limiting on the scope of the present disclosure and appended claims. Additional objects and advantages of the present invention will be appreciated by one of ordinary skill in the art in light of the instant claims, description, and examples and are expressly included within the scope of the present invention.

DETAILED DESCRIPTION

Figure 1:
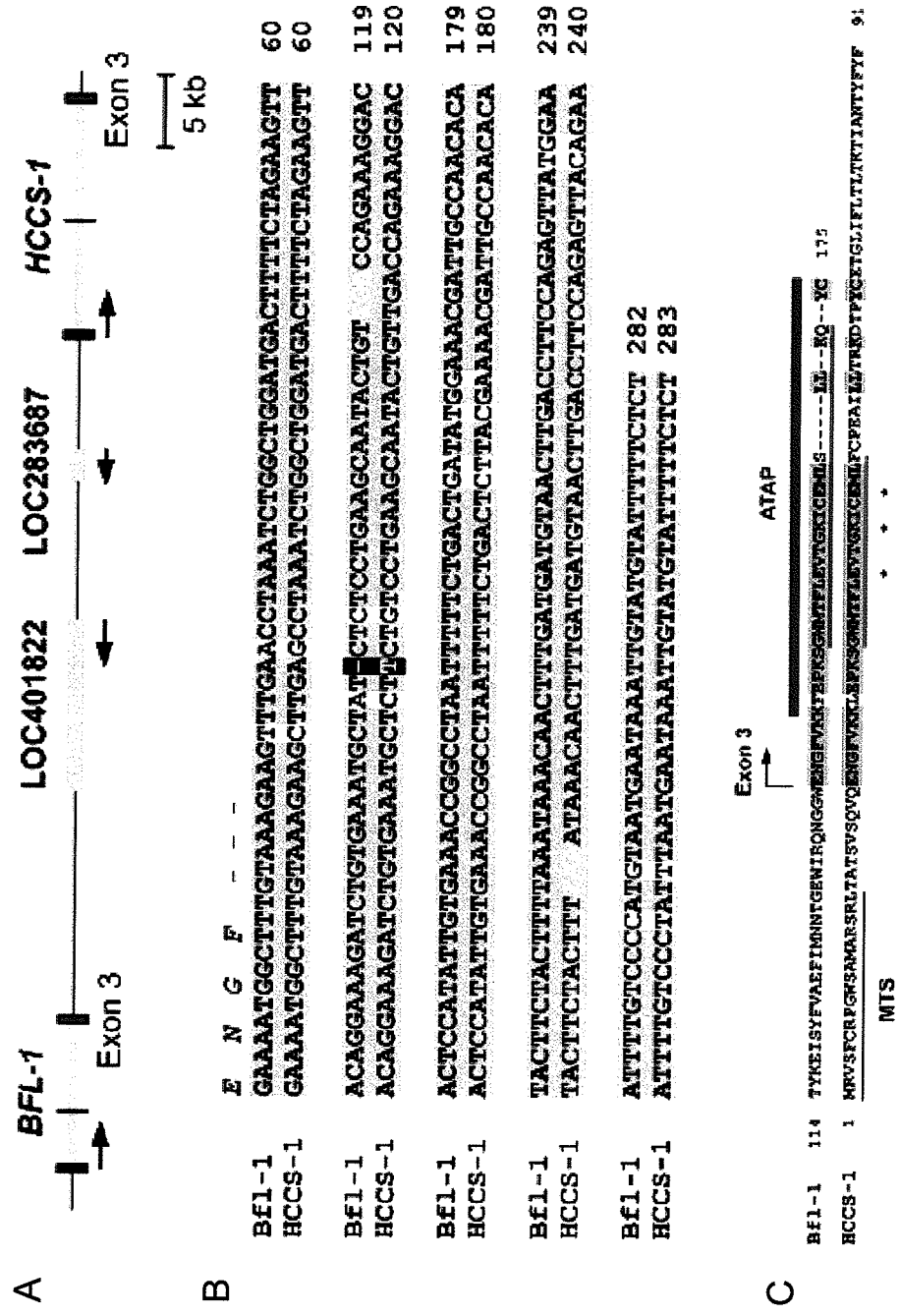
FIG. 1. The amphipathic tailanchoring peptide (ATAP) is conserved in Bfl1 and HCCS1 (See SEQ ID NOs. 2, 3, and 52). (A) Schematic genomic structures of BCL2A1 (BFL-1; SEQ ID NO. 1) and HCCS1 (SEQ ID NO. 54) genes on human chromosome 15q24.3 and 15q25.1, respectively. Black bars indicate exons and red bars indicate conserved exon-3 of BCL2A1 and HCCS1 genes. (B) Alignment of exon-3 sequences from BCL2A1 and HCCS1 genes. Identical sequences are shaded gray and single base gap is shaded black. Stop codons are yellow. (C) Primary sequence comparison of the TA region of Bfl1 and HCCS1. Horizontal red bar indicates the ATAP sequence of Bfl1 and HCCS1. Green lines indicate predicted α-helical regions. Mitochondrial targeting signal (MTS) of HCCS1 is indicated by a blue line. (D) Helix-wheel diagrams of ATAP sequences of Bfl1 and HCCS1. (E) Amino acid sequence alignment of TA regions from human anti-apoptotic Bcl2 family proteins and A1, a mouse homologue of human Bfl1, and ATAP sequences (See SEQ ID NOs. 2-7). F-G: Transient expression of FLAG-TA induced caspase-dependent cell death of HEK 293 cells. Cells were co-transfected with 1.0 μg of the indicated expression plasmids and 0.1 μg of pCMV-β-gal in the absence or presence of 50 μM of pan-caspase inhibitor, OPH. 24 h after co-transfection, cells were stained with propidium iodide (PI) and observed under fluorescence microscope (F). Cell viability was measured by β-galactosidase activity relative to control cells transfected with FLAG mock and the pCMV-β-gal reporter plasmid (G). H: The relative expression levels of the FLAG-tagged proteins and TA peptide were determined by western blotting with an antibody against the FLAG tag epitope.
Figure 1:
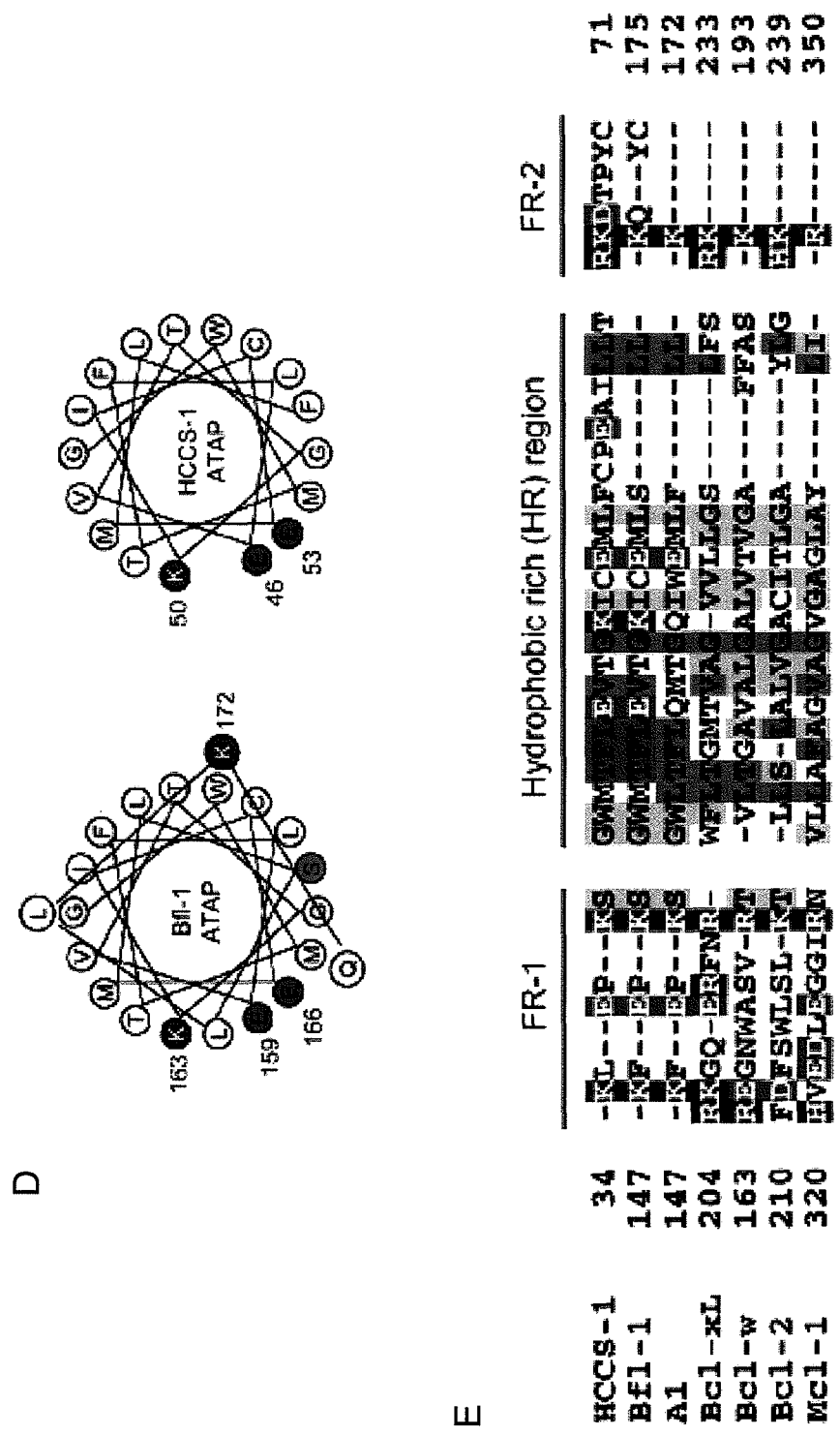
Figure 1:
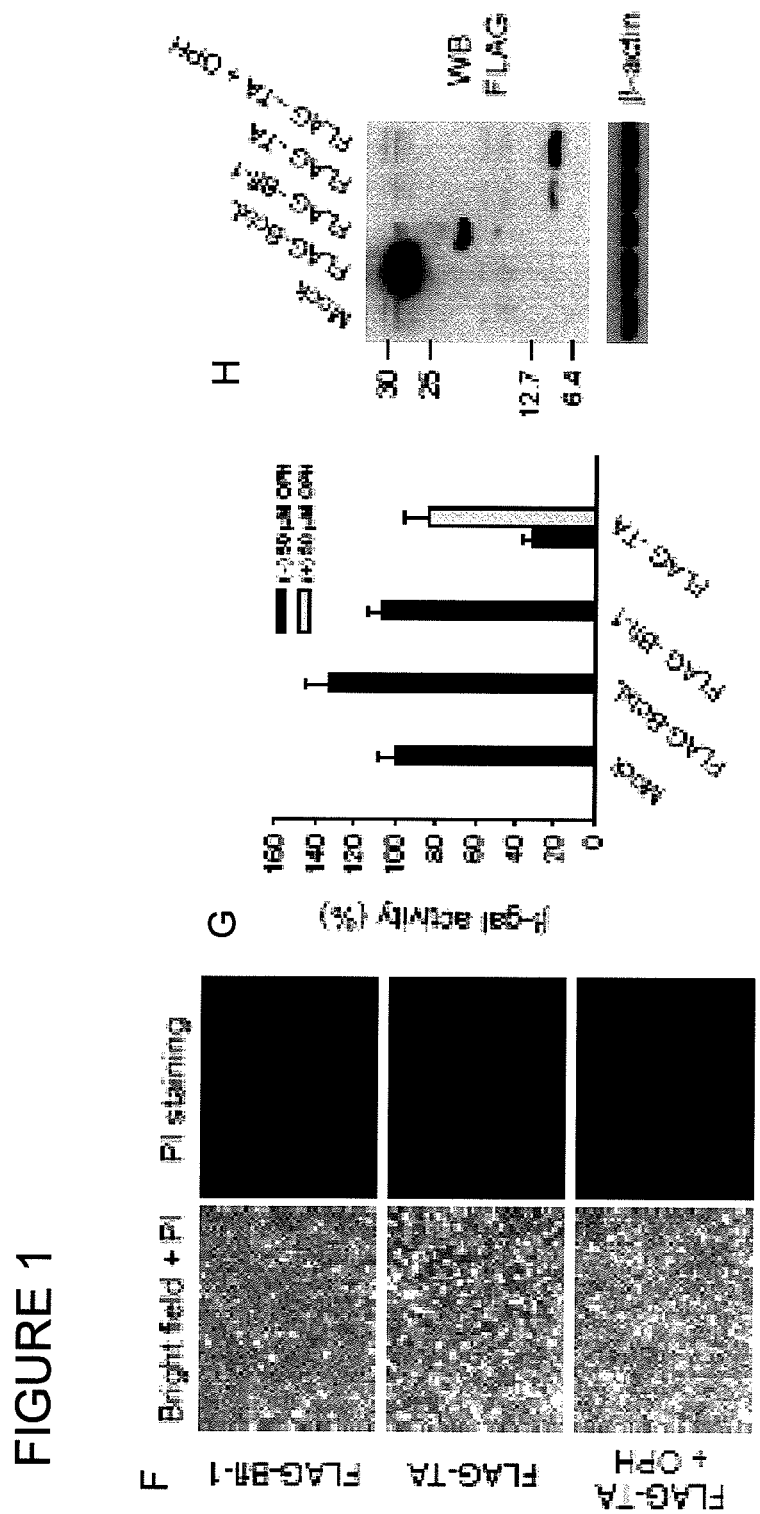

As described herein, ATAP peptides and polypeptides are capable of inducing cellular apoptosis, and therefore, the ATAP gene expression, polypeptide synthesis, activity or protein-protein interactions represent a novel therapeutic intervention for diseases and conditions related dysfunctional cellular proliferation and bacterial infection.

In certain aspects, the present description relates to the subject matter of PCT/KR2004/001324 (WO 2004/110474), Yang et al., *J. Cell. Biochem.*, 94:1234-1247 (2005), and Ko et a., *J. Cell Sci., Aug.* 15; 120(16): 2912-23, which are incorporated herein by reference in their entirety for all purposes.

The present invention provides novel polynucleotides and polypeptides encoded thereby containing an amphipathic tail-anchoring peptide ATAP. The nucleic acid sequences are collectively referred to herein as "ATAP nucleic acids" or "ATAP polynucleotides" and the corresponding encoded polypeptides are referred to interchangably as "ATAP polypeptides," "ATAP peptides," "ATAP proteins," "ATAP-containing polypeptides" or "ATAP-containing proteins." Unless indicated otherwise, "ATAP" is meant to refer to any of the novel nucleic acid or peptide sequences taught or suggested herein. ATAP binding protein," and "ATAP receptor" proteins is meant, a peptide or protein comprising a binding site for an amphipathic tail-anchoring peptide (ATAP) including domains, fusion proteins, chimeras, or fragments thereof.

As used herein, "ATAP receptor gene" or "ATAP receptor structural gene" includes the 5' UTR, 3' UTR, promoter sequences, enhancer sequences, intronic and exonic DNA of the ATAP receptor gene as well as the ATAP receptor gene mRNA or cDNA sequence.

Tail-anchored (TA) proteins, including the Bcl-2 family members, characteristically tether to phospholipid bilayers by a single hydrophobic segment at the carboxyl (C)-terminus with the bulk of the molecule located in the cytosol. Since apoptotic functions of Bcl-2 proteins are linked to their targeting to either ER or MOM, understanding the molecular machinery underlying their subcellular distribution represents a major focus of current research in apoptosis.

Bfl-1 is a human anti-apoptotic Bcl-2 family protein, protecting cells from various apoptotic stimuli including activation of TNF death receptor, treatment of chemotherapeutic drugs and overexpression of Bax or Bid. As described herein, Bfl-1 is bi-functional, in that fusion of EGFP to the amino (N)-terminus of Bfl-1 converts the anti-apoptotic nature of Bfl-1 into a potent pro-apoptotic molecule that targets the mitochondria-dependent apoptosis pathway. Prior to the present description, however, the molecular mechanism responsible for the bi-functional capacity of Bfl-1 was unknown.

The mitochondrial outer membrane (MOM)-targeting tail-anchoring (TA) region often contains a short hydrophobic domain flanked at both end by several positively charged amino acids. Targeting of Bfl-1 to the MOM appears to involve the TA domain, since deletion of 17 amino acids at the C-terminal end caused mis-targeting of Bfl-1 away from the mitochondria. Moreover, Bfl-1S, an alternative splice variant of Bfl-1, with a different C-terminal domain localizes to the nucleus. Because the Bfl-1 TA domain contains three charged residues within the hydrophobic segment that could represent a barrier for stable insertion into the membrane environment, it was widely believed that the carboxyltermi-nus of Bfl-1 could not function as a bona fide TA.

The description and examples presented herein demonstrate a surprising and unexpected MOM targeting and potent pro-apoptotic activity of a short peptide derived from the TA domain of Bfl-1 (i.e., ATAP) (See FIG. 1). The positively charged lysine residues (K147 and K151) are responsible for targeting of the ATAP to the MOM, and the pro-apoptotic activity of the ATAP appears to require the amphiphatic property of TA. Therefore, in one aspect this short peptide can be used as a useful probe for elucidating the molecular events underlying the initiation of mitochondria-dependent apoptosis pathway. In another aspect, ATAP peptide can also be used as a potential therapeutic agent for treatment of proliferative disorders, for example, cancers.

As discussed above, anti-apoptotic Bcl-2 members contain a signature TA motif at their C-termini, consisting of a hydrophobic TMS (18 or 19 amino acids) and two flanking regions (FR-1 and FR-2) containing conserved lysine residues. Distinct from the other members, the TA from Bfl-1 contains charged residues in the middle of TMS producing a unique amphipathic structure. A similar ATAP sequence can be found in another gene, HCCS1, that is not commonly associated with the bcl2 family of genes.

HCCS1, a recently identified tumor suppressor gene whose cellular function has yet to be defined (Kim et al., 2002). The genomic sequence of HCCS1 is located in close proximity to that of Bfl1 on chromosome 15. In addition to ATAP, HCCS1 contains a novel MTS at the N-terminus Since HCCS1 lacking MTS can target to mitochondria and induce caspase-dependent cell death, it suggests that ATAP contributes to the intrinsic mitochondria targeting property for HCCS1. In addition to mitochondria targeting, we also observed parallel changes in the pro-apoptotic activities of ATAP with mutation of the corresponding charged residues in Bfl1 and HCCS1. Our results indicate that the pro-apoptotic function of ATAP is conserved in Bfl1 and HCCS1.

Thus, in one aspect the invention relates to compositions comprising ATAP peptides of the general Formula I: bXaX-buunnnunnanXGbnXann$(X)_{1-6}$nn$(X)_{0-2}$b (I).

Wherein, n=a nonpolar (hydrophobic) amino acid; X=any amino acid; u=polar, uncharged amino acid; b=basic amino acid; and a=acidic amino acid.

In yet another aspect the invention relates to compositions comprising ATAP peptides of the general Formula (II): (K/R)n(E/D)(P)(K/R)SGW(M/L)(S/T)FL(E/D)nTG-(K/R)I (X)(E/D)ML$(X)_{1-6}$LL$(X)_{0-2}$(K/R) (II). Wherein, n, X, u, b, and a are defined as above.

As used herein, basic amino acids include: Histidine, Arginine, and Lysine; acidic amino acids include: Aspartate, and Glutamate; nonpolar (hydrophobic) amino acids include: Phenylalanine, Alanine, Leucine, Methionine, Isoleucine, Tryptophan, Proline, and Valine; polar, uncharged amino acids include: Cysteine, Glycine, Glutamine, Asparagine, Serine, Tyrosine, and Threonine.

Here we demonstrate that ATAP peptides display potent pro-apoptotic activities that result from two conserved functional motifs, one that allows targeting to mitochondrial membrane and the other that provides an amphipathic property to the peptide. ATAP can induce mitochondria permeability transition and act as a potent stimulator of apoptosis. Although all anti-apoptotic Bcl2 members contain the TA signature motif at their C-termini, ATAPs of Bfl1 and HCCS1 are unique as they contain three charged residues in the middle of the hydrophobic-rich region and therefore are amphipathic in nature. The 29 amino acid ATAP is sufficient for localizing a reporter molecule (EGFP) at mitochondria. Our results reveal that three basic amino acids within flanking regions determine specificity for targeting to mitochondria. The mFR4 mutant (K147L/K151L) only partially localizes to the mitochondria and primarily resides in the cytoplasm. In addition, mutations of three lysine residues within FR-1 and FR-2 lead to complete mis-localization of TA from the mitochondria (Linker-mFR-7).

Previously, the ATAP of Bfl1 has been excluded as a bona fide TA on the premise that the existence of charged residues represents a barrier for penetration and partition of the peptide to lipid bilayer membranes (Cory and Adams, 2002; Gross et al., 1999). Here we demonstrate that ATAP is sufficient for localizing a reporter molecule (GFP) at mitochondria. Our results further reveal that three basic residues, for example, lysine or arginine, within the FR-1 and FR-2 regions (FIG. 1) are critical for targeting to mitochondria. The amphipathicity of TMS from Bfl-1 and HCCS-1 are unique among all known tail-anchored proteins, including the anti-apoptotic Bcl-2 family proteins. Interestingly, an external sequence containing basic residues adjacent to the N-terminus of TA could also function as a pseudo-flanking region for mitochondrial targeting in the absence of basic residues within the Bfl1 flanking regions. This indicates that the position of basic residues at the N-terminus of ATAP is essential for efficient mitochondrial targeting.

Figure 7:
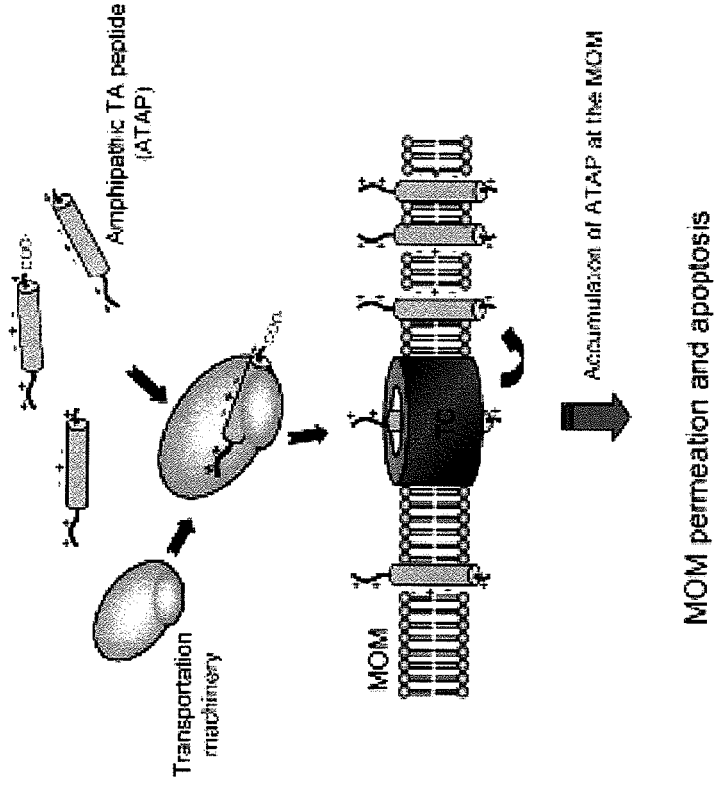
FIG. 7. Schematic diagram to illustrate the pro-apoptotic activity of TA. TA domain derived from Bfl-1 can induce apoptosis by targeting to the mitochondrial outer membrane (MOM) through specific intracellular transportation machinery. The presence of charged residues in the middle of the tail-anchoring (TA) sequence bestow an amphipathic helical feature on the transmembrane segment, and is likely involved in the perturbation of mitochondria membrane potential. (TC=translocation complex).

Charged residues located within the hydrophobic rich (HR) domain are essential for the pro-apoptotic activity of ATAP. Without being limited to any particular theory, the inventors propose that these charged amino acids (E159, K163 and E166 in Bfl1 ATAP; and E46, K50, and E53 in HCCS1 ATAP) are involved in oligomerization, and perhaps, the formation of an aqueous pore to perturb mitochondrial membrane integrity (See FIGS. 1 and 7). In addition, the inventors postulate that the charged residues (for example, E159, K163 and E166), which face one side of the alpha-helix, can participate in the formation of an aqueous ion-conduction pore, and therefore, perturbs mitochondria permeability transition. This is supported by our finding that ATATP peptide can alter the ion permeability of reconstituted lipid bilayers. We have extensive data suggesting that the Bfl-1 ATAP itself is likely responsible for the potent pro-apoptotic activity, because similar effects were observed with FLAG-TA and EGFP-TA, in both biochemical, cell biological and imaging assays.

Using the lipid bilayer reconstitution system, we demonstrated that the synthetic wild-type ATAPpeptide produced significant effects to the cation permeability of the lipid bilayer membrane, whereas a mutant mHR7 peptide, which can bind to the mitochondria membrane but is not toxic to the cells, did not affect conductance of the lipid bilayer membrane. The ATAP-mediated permeability changes in the in vitro system did not display the typical stable conductance behavior one would expect from a pore-forming channel. ATAP could either interact with or modulate the pre-existing channels to alter mitochondrial membrane permeability, or potentially other domains of the Bfl1 or HCCS1 proteins may contribute to changes in membrane permeability observed in vivo.

Two general types of peptides known to trigger mitochondrial apoptosis are currently under clinical trials as potential cancer therapeutic reagents. One type is the amphipathic peptides containing a high content of basic residues derived from antibacterial peptides (Chen et al., 2001; Ellerby et al., 1999; Mai et al., 2001). Targeting of these peptides to mitochondria relies on the electrostatic interaction between positively charged residues in the peptides and negatively charged mitochondrial membrane lipids. After targeting to the mitochondrial membrane, these peptides disrupt mitochondrial function and cause cytochrome c release through deformation of lipid membrane or formation of pores at the mitochondrial membrane. This mechanism may be similar to their antimicrobial function on negatively charged bacterial membrane (Shai and Oren, 2001). However, since the cytotoxic activity of these peptides depends on a high intracellular concentration of peptides, because of inefficient targeting to mitochondria, their specificity in targeting cancer cells must be maximized to allow effective clinical application.

The other class of peptides are those derived from BH3-only pro-apoptotic Bcl2 family proteins such as Bad and Bid (Letai et al., 2002; Schimmer et al., 2001; Walensky et al., 2004). The BH3 peptide of Bid can directly bind to pro-apoptotic Bax and Bak to activate them to induce apoptosis, or can bind to anti-apoptotic Bcl2 and Bcl-xL to prevent their inhibition of Bax and Bak (Letai et al., 2002). A recent study showed that a stabilized BH3 peptide derived from Bid could specifically induce apoptosis of several leukemia cells, highlighting their therapeutic potential (Walensky et al., 2004). However, downregulation of proapoptotic protein and/or upregulation of anti-apoptotic protein often provides cancer cells with a resistance mechanism against apoptotic therapeutics.

Since the full-length Bfl1 and HCCS1 have opposite functions, one being anti-apoptotic and the other being proapoptotic, it is interesting to observe their expression levels in various tissues. Analyses of the available mRNA microarray data and EST expression profiles reveal that the expression of BCL2A1 and HCCS1 are mutually exclusive in 16 out of 19 tissues examined, suggesting their possible complementary tissue-specific functions in cell proliferation and regeneration. Interestingly, only the lymph node and kidney were found to contain high level transcripts of both Bfl1 and HCCS1. This result suggests that Bfl1 might share similar biological functions to HCCS1 as a pro-apoptotic factor to achieve dynamic regulation of apoptosis according to cell state at the lymph node and kidney. In support of this hypothesis, Kucharczak et al. (Kucharczak et al., 2005) found that Bfl1 can be converted to pro-apoptotic factor by proteolytic turnover in a FL5.12 pro-B cell line in response to TNFα stimulation, indicating that the pro-apoptotic activity of Bfl1 might be involved during the B-cell selection process that occurs in lymph nodes.

In an attempt to examine the tumor-suppressor function of HCCS1, we used RT-PCR to examine the expression level of HCCS1 in normal human tissues including lung, breast and cervix, and in various well established cancer cell lines. To discriminate HCCS1 and BCL2A1 transcripts, we used primer pairs specific to the exon 1 region of HCCS1 and BCL2A1. In the normal lung, breast and cervix tissues, abundant HCCS1 products were detected whereas BCL2A1 products were conspicuously absent, which is consistent with the microarray data, which showed that these tissues contain abundant levels of HCCS1 but not Bfl1. Interestingly, a very low expression level of HCCS1 was detected in two of six breast cancer cell lines, e.g. MDA-MB231 and MDA-MB435, indicating a possible role for HCCS1 in tumorigenesis. It is noticeable that HeLa—a cervical cancer cell line—also displayed reduced expression of HCCS1. Whether downregulation of HCCS1 is directly involved in the development of cancer cells, and whether altered targeting of HCCS1 plays a role in its pro-apoptotic function, need to be examined further.

Our results indicate that ATAP can also act as a potent antibiotic. Expression of ATAP in *E. coli* leads to lysis of the cells whenever high levels of expression were accomplished. This indicates that at amphpatic capacity of ATAP can not only disrupt MOM permeation, but it can also produce similar effects in the bacterial membrane that has a similar lipid composition. Generally, the eukaryotic cell plasma membrane will not be affected by these type of peptides because of differences in membrane composition. Thus, ATAP has a useful application as an antibaterical agent that could be used to treat various bacterial infections throughout the body. Additionally, since this appears to be a physical disruption of membrane permeability, this antibiotic effect would be less likely to lead to antibiotic resistance that can often result from the use of antibiotics that target a metabolic pathway ATAP peptides can be used as potent reagent the treatment of cancers, hyperplasias, and bacterial infections. ATAP is distinguished from the cationic antibacterial peptides by active and specific targeting to the mitochondrial membrane (in eukaryotic cells). ATAP is unique from BH3 peptides because of its direct interaction with the mitochondria membrane, which does not require participation of the Bcl2 family proteins. Anti-apoptotic Bcl-xL cannot block ATAP-induced apoptosis and the pro-apoptotic activity of Bax or Bak is not required for the pro-apoptotic function of ATAP. Therefore, ATAP has the potential to overcome the resistance of cancer cells to apoptotic stimuli generated by altered expression levels of Bcl2 family proteins. Here we describe a new strategy for developing cancer therapeutic reagents using the ATAP sequence, which can specifically target mitochondria to disrupt mitochondrial membrane integrity.

Figure 3:
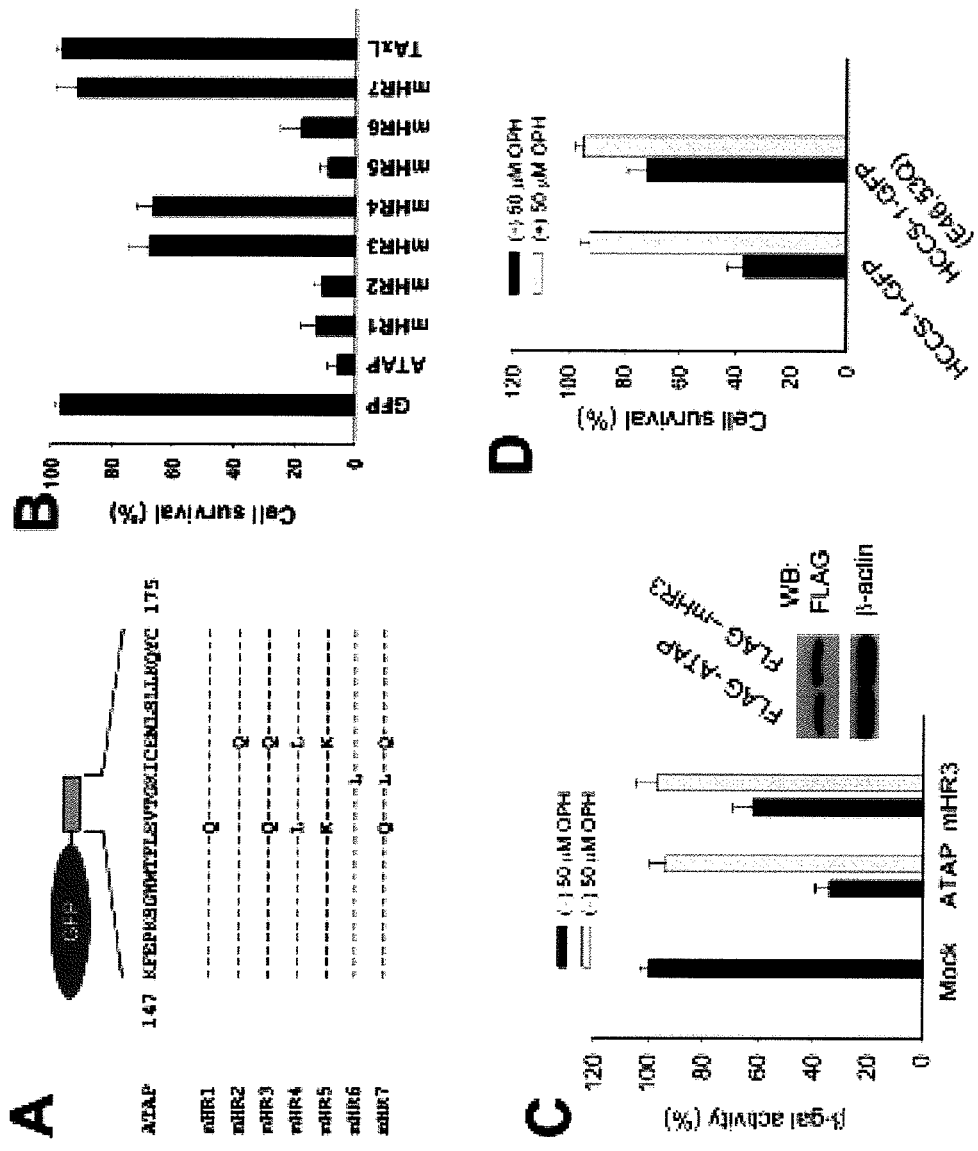
FIG. 3. The pro-apoptotic activity of ATAP requires an amphipathic property. (A) Schematic representation of the GFP-ATAP constructs (SEQ ID NOs. 45-51) in which point mutations were introduced into the hydrophobic rich (HR) region of the ATAP. (B) Cell survival was measured by PI exclusion in the HEK293 cells transfected with 1 μg GFP-ATAP mutant constructs 24 hours after transfection. (C) Flag-mHR3 peptide showed reduced proapoptotic activity. HEK293 cells were co-transfected with 0.1 μg pCMV-β-gal reporter plasmid and 1 μg of the Flag-ATAP or Flag-mHR3 expression plasmids. 24 hours after co-transfection, cell viability was measured by β-galactosidase activity (left). The relative expression levels of the Flag-tagged peptides were determined by western blotting with an antibody against the Flag tag epitope (right). (D) Involvement of amphipathic nature of ATAP in the apoptotic function of HCCS1. HEK293 cells were co-transfected with 0.1 μg pCMV-β-gal reporter plasmid and 1.0 μg HCCS1-GFP or HCCS1-GFP (E46Q/E53Q) containing mutations corresponding to mHR3 of the Bfl1 ATAP. 24 hours after cotransfection, cell viability was measured by β-galactosidase activity. Data are expressed as the mean±s.e.
Figure 5:
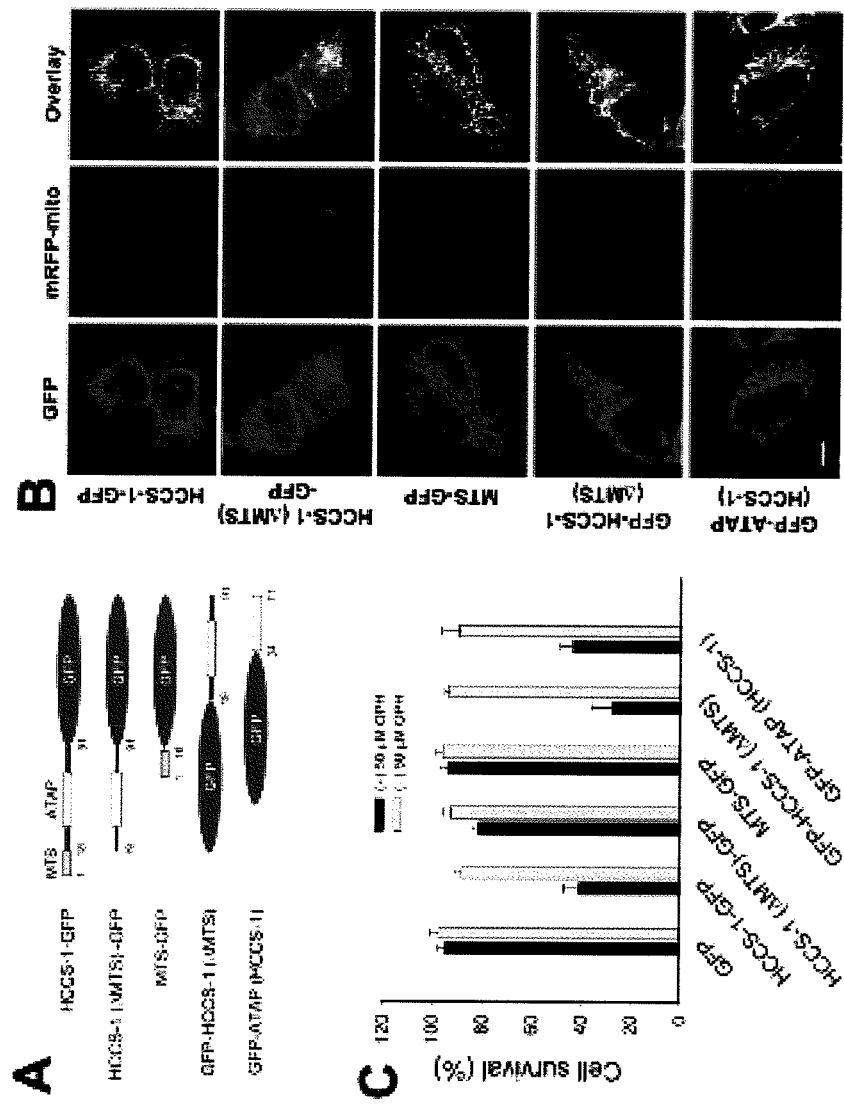
FIG. 5. Both MTS and ATAP are involved in mitochondrial-targeting apoptosis induced by HCCS1. (A) Schematic representation of the GFP fusion proteins of HCCS-1 and its deletion mutants. (B) Subcellular localization of GFP fusion proteins. HeLa cells were transfected with 0.5 μg of the indicated plasmids. Cell culture was performed in the presence of 50 µM OPH. 18 hours after transfection, cells were incubated in medium containing 50 nM MitoTracker for 2 hours and fixed using 4% paraformaldehyde. Localization of GFP fusion proteins was observed using confocal microscopy. Bar, 10 µm. (C) Cell survival was measured by PI exclusion in the HEK293 cells transfected with 1 µg GFP fusion constructs 24 hours after transfection.

As such, a novel approach for the treatment or proliferative disorders or bacterial infections utilizes ATAP and its proapoptotic mutants. While not being limited to any particular theory, the data supports a direct role of ATAPs, at least in eukaryotic cells, in the disruption of the mitochondrial membrane potential; and induction of apoptosis. This model is supported by two critical pieces of evidence. First, although the two negatively charged residues (E159 and E166) in the middle of the Bfl-1 TMS are important for pro-apoptotic activity of the Bfl-1 TA, mHR5 with positively charged residues (E159K/E166K) also has potent pro-apoptotic activity comparable to wild type TA (FIG. 3 and FIG. 5). This implies that the amphipathicity of the TMS plays a critical role for pro-apoptotic activity of the Bfl-1 TA rather than specific charge interactions of E159 and E166 residues with other intermolecular amino acid residues. Second, in our attempt to generate bacterially expressed recombinant TA we used two kinds of bacterial TA expression vectors. In both cases, we observed that the expression of the Bfl-1 TA peptide was toxic to *E. coli* cell growth (data not shown). Since membranes from gram-negative bacteria, such as *E. coli*, contain a high content of negatively charged lipids much like the mitochondrial membrane, the toxic effect of TA could result from direct action on lipid membranes. Together these results suggest the possibility that the ATAP peptides can directly damage the lipid structure of the MOM after targeting to the MOM.

Figure 2:
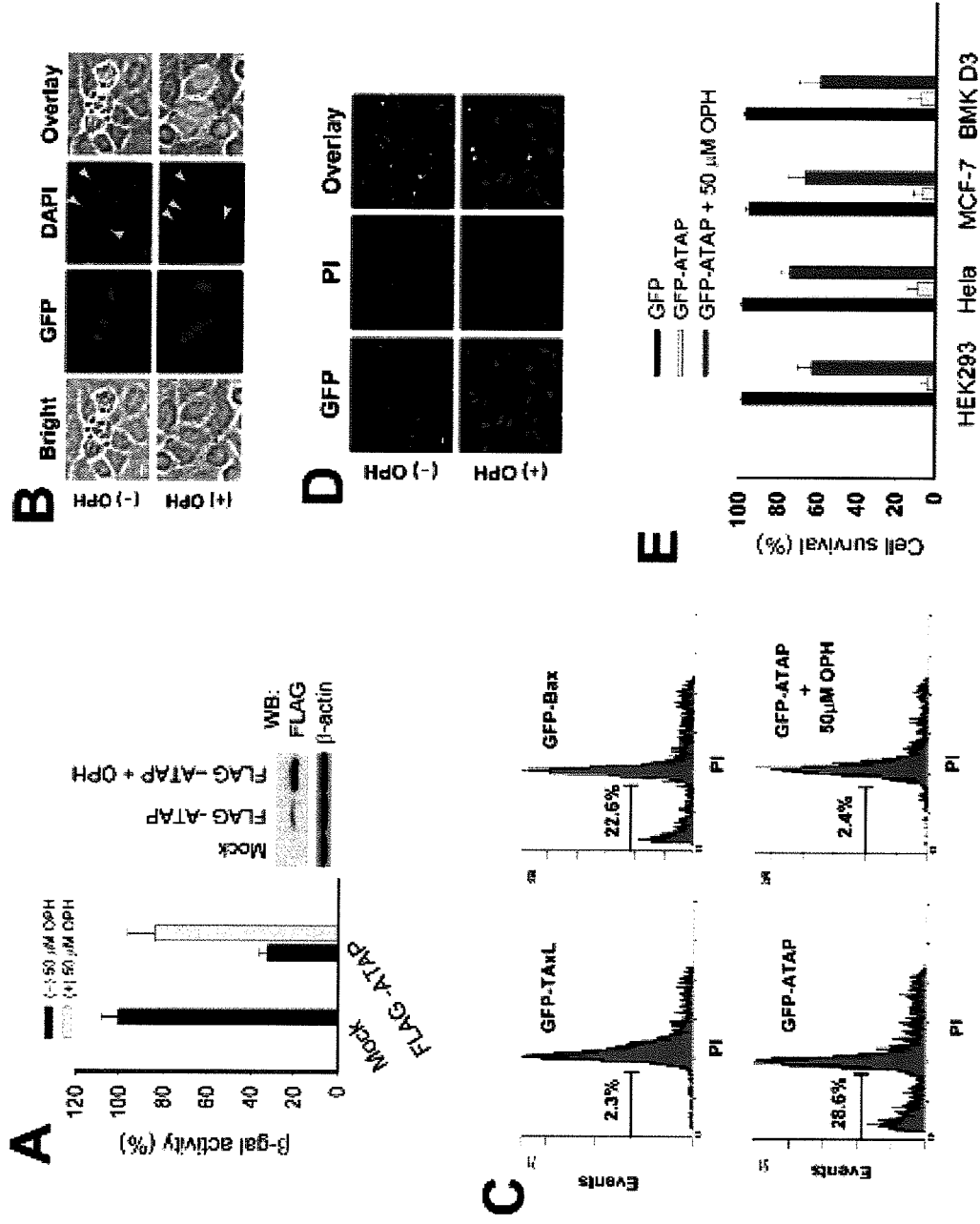
FIG. 2. ATAP-induced apoptosis is independent of Bax and Bak activities. (A) Transient expression of Flag-ATAP induced caspase-dependent cell death of HEK293 cells. Cells were co-transfected with 1 μg of mock or Flag-ATAP expression plasmid with 0.1 μg pCMV-β-gal in the absence or presence of 50 μM OPH. Cell viability was measured by β-galactosidase activity relative to control cells transfected with mock plasmid and the pCMV-β-gal reporter plasmid (left). The relative expression levels of the Flag-ATAP peptide was determined by western blotting with an antibody against the Flag tag epitope (right). (B,C) Transient expression of GFP-ATAP-induced apoptotic nucleus morphology and sub-G1 population in a caspase-dependent manner. GFP-ATAP-transfected HeLa cells were fixed, stained with DAPI and observed under fluorescence microscope 24 hours after transfection (B). HEK293 cells were transiently transfected with the indicated expression plasmids. 18 hours after transfection, cells were harvested, fixed, and stained with PI. The DNA content of GFP-positive cells was then analyzed by flow cytometry (C). (D) Transient expression of GFP-ATAP induced acute cell death in a variety of cancer cells, including HEK293, HeLa, caspase-3 deficient MCF-7 cells and BMK D3 cells derived from the kidney of neonatal knockout mice for Bax and Bak genes. 24 hours after transfection, cell survival was measured by PI exclusion. Representative images taken from HEK293 cells are shown. (E) The percentage of surviving cells was determined by the ratio of PI-negative cells to total GFP-positive cells. About 300 cells from three different fields were scored. Data are expressed as the mean±s.e. Bars, 10 μm.

The ATAPs of the invention are distinguished from the cationic amphipatic peptides derived from currently known anti-bacterial peptides by active and specific targeting to the MOM. Furthermore, ATAPs are also distinguished from BH3 peptides by its direct toxic effect on the MOM that does not require interaction with Bcl-2 family proteins. Anti-apoptotic Bcl-xL and Bfl-1 could not block apoptosis induced by the Bfl-1 TA and the pro-apoptotic activity of Bax or Bak was not required for ATAP pro-apoptotic activity (FIG. 2).

Therefore, the ATAPs have potential to overcome the resistance of cancer cells to apoptotic stimuli generated by modulating the level of the Bcl-2 family proteins, and also the potential to overcome the problem of bacterial resistance to currently known classes of antibiotics (e.g., glycosides, sporins, glycopeptides, macrolides, sulfonamides, and the like). As such, the present invention represents a novel strategy for developing cancer therapeutic peptide using the pro-apoptotic ATAP peptide that can specifically target mitochondria and disrupt mitochondrial membrane integrity. Furthermore, the ATAP containing polypeptides can be used as antibacterials, alone or in conjunction with existing antibacterial agents.

In certain embodiments, polypeptide compositions of the invention that comprise ATAP peptides are from about 25 amino acids in total length to about 300 amino acids in total length. In a preferred embodiment the polypeptide compositions of the invention comprising ATAP peptides are from about 26 to about 100, 90, 80, 70, 60, 50, 40, or 30 amino acids in total length.

In another aspect, the invention provides an isolated ATAP nucleic acid molecule encoding a ATAP polypeptide that includes a nucleic acid sequence that has at least 30%, 40%, 50%, 60%, 70%, 80%, 90% or 100% identity to the nucleic acid disclosed in SEQ ID NO: 37 or 59. In certain embodiments, the isolated ATAP nucleic acid molecule will hybridize under stringent conditions to a nucleic acid sequence complementary to a nucleic acid molecule that includes a protein-coding sequence of a ATAP nucleic acid sequence. The invention also includes an isolated nucleic acid that encodes a ATAP polypeptide, or a fragment, homolog, analog, fusion protein, pseudopeptide, peptidomimetic or derivative thereof. For example, the nucleic acid can encode a polypeptide having at least 30%, 40%, 50%, 60%, 70%, 80%, 90% or 100% identity to an ATAP region from Bfl-1 or HCCS1. In certain embodiments, the polypeptide of the invention comprises a peptide of at least one of SEQ ID NOS: 36, 38-51, 53 or combinations thereof.

Nucleic acids contemplated by the invention can be, for example, a genomic DNA fragment or a cDNA molecule that contains a nucleic acid sequence having at least 30%, 40%, 50%, 60%, 70%, 80%, 90% or 100% identity to an ATAP region from Bfl-1 or HCCS1 (SEQ ID NOs. 37 and 59). In certain embodiments, the nucleic acids of the invention comprises a polynucleotide of at least one of SEQ ID NOs: 37 and 59.

Also included in the invention is an oligonucleotide, e.g., an oligonucleotide which includes at least 6 contiguous nucleotides of a ATAP nucleic acid (e.g., SEQ ID NO: 37 or 59) or a complement of said oligonucleotide.

Also included in the invention are substantially purified ATAP polypeptides, for example, ATAP peptides of the general Formula I:

$$bXaXbuunnunnanXGbnXann(X)_{1-6}nn(X)_{0-2}b \qquad (I).$$

Wherein, n=a nonpolar (hydrophobic) amino acid; X=any amino acid; u=polar, uncharged amino acid; b=basic amino acid; and a=acidic amino acid.

In additional embodiments, the invention includes ATAP peptides of SEQ ID NOS: 36, 38-51, 53 or combinations thereof. In certain embodiments, the ATAP polypeptides include an amino acid sequence that is substantially identical to the amino acid sequence of a human Bfl-1 or HCCS1 ATAP polypeptide.

The invention also features antibodies that immunoselectively-bind to ATAP polypeptides, or fragments, homologs, analogs, pseudopeptides, peptidomimetics or derivatives thereof.

In another aspect, the invention includes pharmaceutical compositions that include therapeutically- or prophylactically-effective amounts of a therapeutic nucleic acid, polypeptide, and a pharmaceutically-acceptable carrier. The therapeutic can be, e.g., an ATAP nucleic acid, for example, a peptide nucleic acid, a cDNA, or RNA, such as for example, a small inhibitory RNA; an ATAP polypeptide; or an antibody specific for an ATAP polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes an endogenous or exogenously expressed ATAP nucleic acid, under conditions allowing for expression of the ATAP polypeptide encoded by the DNA. If desired, the ATAP polypeptide can then be recovered.

In still another aspect the invention includes a method of producing a polypeptide by culturing a cell that contains an exogenous ATAP nucleic acid disposed upstream or downstream of an endogenous, exogenous, or heterologous promoter. In certain embodiments, the exogenous promoter is incorporated into a host cell's genome through homologous recombination, strand break or mismatch repair mechanisms. In certain embodiments, expression of the exogenous ATAP gene is under the control of a tissue-specific or chemically inducible promoter.

In another aspect, the invention encompasses nucleic acids encoding ATAPs in which the nucleic acid comprises, in addition to the polynucleotide encoding an ATAP, a polynucleotide portion that encodes an ATAP inhibitor polypeptide such that the inhibitor is able to mask the cytotoxic effect of ATAP until the desired moment. In one exemplary embodiment, the inhibitory polypeptide may be linked to the ATAP by a protease cleavage site. Upon exposure of the cell to a particular stimulus, the protease is activated; releasing the inhibitory polypeptide from the ATAP polypeptide—the "free" ATAP polypeptide is then able to induce apoptosis in the cell. In still another embodiment, the ATAP inhibitor is a chemical moiety, such as a small molecule, that can similarly be cleaved from the ATAP polypeptide, emzymatically, to allow ATAP to induce apoptosis.

In another aspect, the invention includes a method of detecting the presence of a ATAP polypeptide in a sample. In the method, a sample is contacted with a compound that selectively binds to the polypeptide under conditions allowing for formation of a complex between the polypeptide and the compound. The complex is detected, if present, thereby identifying the ATAP polypeptide within the sample.

The invention also includes methods to identify specific cell or tissue types based on their expression of a ATAP nucleic acid, polypeptide or ATAP fusion polypeptide.

In additional embodiments the invention includes fusion proteins comprising a "tag" or indicator portion and an ATAP portion, and nucleic acids encoding the same. In certain aspects the tag or indicator portion can be a peptide adapted for purification purposes, for example, FLAG tag, 6xHis tag or the like. In other aspects, the tag peptide comprises a peptide adapted for providing a signal such as an antibody epitope or a fluorescent peptide. Still other aspects include the fusion of the ATAP with a peptide that is adapted for mediating activation, subcellular localization or translocation across a cellular membrane, for example, a TAT fusion protein from the HW virus.

Also included in the invention is a method of detecting the presence of a ATAP nucleic acid molecule in a sample by contacting the sample with a ATAP nucleic acid probe or primer, and detecting whether the nucleic acid probe or primer bound to a ATAP nucleic acid molecule in the sample.

In a further aspect, the invention provides a method for modulating the activity of a ATAP polypeptide by contacting a cell sample that includes the ATAP polypeptide with a compound that binds to the ATAP polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of an ATAP as a therapeutic in the manufacture of a medicament for treating or preventing disorders or syndromes including, e.g., cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, autoimmune disease, lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological disesases, hypercalceimia, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, alopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Ostoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer; neoplasias, e.g., BPH; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

The therapeutic composition of the invention comprises, in certain embodiments, for example, an ATAP nucleic acid; a nucleic acid that binds an ATAP encoding nucleic acid; an ATAP polypeptide, peptide analog, pseudopeptide or peptidomimetic based thereon; a small molecule modulator of ATAP or a ATAP protein-protein interaction; or a ATAP-specific antibody or biologically-active derivatives or fragments thereof. As described herein, ATAP mediates the induction of cellular apoptosis. Therefore, targeting the expression and/or activity of these nucleic acids, polypeptides, and homologs thereof will allow for a novel treatment of various acute and chronic diseases and conditions, for example, those related to proliferative dysfunction.

The invention includes methods for the treatment of or amelioration of diseases and/or disorders related to cell proliferation comprising administering an effective amount of the composition of the invention to a subject in need thereof. In certain embodiments, the invention comprises methods for treating cancer, of any type, comprising administering an effective amount of the therapeutic composition of the invention to a subject in need thereof. In any of the embodiments described herein, the therapeutic composition of the invention may comprise ATAP encoding nucleic acids, ATAP polypeptides, fusion proteins, pseudopeptides, or the like; together with a pharmaceutically acceptable carrier.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle damage due to a myocardial infarction, sclerotic lesion, or muscle tear due to sports-related activity to promote the regeneration and repair of the damaged muscle tissue. Such pharmaceutically acceptable carriers and excipients and methods of administration will be readily apparent to those of skill in the art.

Polypeptides of the invention can be used as immunogens to produce antibodies specific for the invention, and as vaccines. They can also be used to screen for potential agonist and antagonist compounds. In addition, a cDNA encoding ATAP may be useful in gene therapy, and ATAP may be useful when administered to a subject in need thereof. By way of non-limiting example, the compositions of the present invention will have efficacy for treatment of patients suffering from the diseases and disorders disclosed above and/or other pathologies and disorders of the like. In addition, the invention relates to nucleic acids, including interfering nucleic acids, and polypeptides encoding ATAP interacting proteins.

The invention further includes a method for screening for a modulator of disorders or syndromes including, e.g., the diseases and disorders disclosed above and/or other pathologies and disorders of the like. The method includes contacting a test compound with a ATAP polypeptide and determining if the test compound binds to said ATAP polypeptide. Binding of the test compound to the ATAP polypeptide indicates the test compound is a modulator of activity, or of latency or predisposition to the aforementioned disorders or syndromes.

Also within the scope of the invention is a method for screening for modulators of Bfl-1 or HSSC1 activity, comprising providing a library of small molecule compounds and screening for binding to an ATAP. Binding of the compound to a ATAP polypeptide indicates a potential modulator of Bfl-1 or HSSC1 activity. In other aspects, the invention includes methods for evaluating the therapeutic potential of such compounds comprising administering the ATAP binding molecule to a test subject, for example, a cell or in tact animal, and measuring the activity or ability of the compound to induce or inhibit apoptosis in the test subject versus a control. Next, the activity in the test animal and the control animal is compared. A change in the activity in the test animal relative to the control animal indicates the test compound is a modulator of the disorder or syndrome.

In yet another aspect, the invention includes a method for determining the presence of or predisposition to a disease associated with alterations in the type or levels of an ATAP-containing polypeptide, nucleic acid, or both, in a subject (e.g., a human subject). The method includes determining the sequence of the ATAP polypeptide in a test sample from the subject and comparing the genotype or haplotype in the test sample to that of a control or reference sequence. An alteration in the genotype of the ATAP polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various disorders as well as to determine the stage of particular disorders.

In a further aspect, the invention includes a method of treating or preventing a pathological condition associated with a disorder in a mammal by administering to the subject a ATAP polypeptide, a ATAP nucleic acid, or a ATAP-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

In yet another aspect, the invention can be used in a method to identity the cellular receptors and downstream effectors of the ATAP-containing polypeptide by any one of a number of techniques commonly employed in the art. These include but are not limited to the two-hybrid system, affinity purification, co-precipitation with antibodies or other specific-interacting molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the term "ATAP antagonist" or "antagonist of ATAP" is used generally to refer to an agent capable of direct or indirect inhibition of ATAP expression, translation, and/or activity. Also, as used herein "ATAP receptor" relates generally to any protein or fragment thereof capable of undergoing binding to a ATAP protein.

In certain aspects, the modulation of ATAP activity is accomplished by, for example, the use of or modulation of ATAP binding partners, i.e., factors that bind to ATAP and neutralize its biological activities, such as neutralizing anti-ATAP, ATAP receptors, ATAP receptor fragments, and ATAP receptor analogs; the use of ATAP-receptor antagonists, such as antibodies, pseudopeptides, peptide analogs or peptidomimetics that bind and disrupt the ATAP-receptor interaction; small molecules that inhibit ATAP activity or intermolecular interactions, or alter the normal configuration of ATAP, or inhibit productive ATAP/ATAP-receptor binding; or the use of nucleotide sequences derived from ATAP gene and/or ATAP receptor gene, including coding, non-coding, and/or regulatory sequences to prevent or reduce ATAP expression by, for example, antisense, ribozyme, and/or triple helix approaches.

In another aspect the present invention provides a kit comprising a suitable container, the ATAP nucleic acid or polypeptide of the invention, and instructions for its use.

In another aspect, the invention relates to a method for diagnosing or monitoring disorder or disease or progression comprising detecting for the presence of a nucleotide polymorphism in the ATAP portion of Bfl-1 or HCCS1, through the detection of the expression level of a ATAP region or a ATAP receptor gene or protein or both. Polymorphisms have been identified that correlate with disease severity. (See, Zhong et al., *Nucleic Acids Res.* 2005 Aug. 2; 33(13):e121; Donn et al., *Arthritis Rheum.* 2004 May; 50(5):1604-10; all of which are incorporated herein by reference in their entirety for all purposes.).

As one of ordinary skill will comprehend, ATAP, and ATAP receptor gene polymorphisms associated with diseases are useful as diagnostic markers according to the methods of the invention may appear in any of the previously named nucleic acid regions. Techniques for the identification and monitoring of polymorphisms are known in the art and are discussed in detail in U.S. Pat. No. 6,905,827 to Wohlgemuth, which is incorporated herein by reference in its entirety for all purposes.

Certain aspects of the invention encompass methods of detecting gene expression or polymorphisms with one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression or polymorphisms. Such sequences may be predictive of a disease state.

Diagnostic Oligonucleotides of the Invention

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

In certain aspects, the invention relates to diagnostic oligonucleotides and diagnostic oligonucleotide set(s), for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In the context of the invention, nucleic acids and/or proteins are manipulated according to well known molecular biology techniques. Detailed protocols for numerous such procedures are described in, e.g., in Ausubel et al. Current Protocols in Molecular Biology (supplemented through 2000) John Wiley & Sons, New York ("Ausubel"); Sambrook et al. Molecular Cloning-A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger").

Genotyping

In addition to, or in conjunction with the correlation of expression profiles and clinical data, it is often desirable to correlate expression patterns with the subject's genotype at one or more genetic loci or to correlate both expression profiles and genetic loci data with clinical data. The selected loci can be, for example, chromosomal loci corresponding to one or more member of the candidate library, polymorphic alleles for marker loci, or alternative disease related loci (not contributing to the candidate library) known to be, or putatively associated with, a disease (or disease criterion). Indeed, it will be appreciated, that where a (polymorphic) allele at a locus is linked to a disease (or to a predisposition to a disease), the presence of the allele can itself be a disease criterion.

Numerous well known methods exist for evaluating the genotype of an individual, including southern analysis, restriction fragment length polymorphism (RFLP) analysis, polymerase chain reaction (PCR), amplification length polymorphism (AFLP) analysis, single stranded conformation polymorphism (SS CP) analysis, single nucleotide polymorphism (SNP) analysis (e.g., via PCR, Taqman or molecular beacons), among many other useful methods. Many such procedures are readily adaptable to high throughput and/or automated (or semi-automated) sample preparation and analysis methods. Most, can be performed on nucleic acid samples recovered via simple procedures from the same sample as yielded the material for expression profiling. Exemplary techniques are described in, e.g., Sambrook, and Ausubel, supra.

The invention also features nucleic acid molecules, for example enzymatic nucleic acid molecules, antisense nucleic acid molecules, decoys, double stranded RNA, triplex oligonucleotides, and/or aptamers, and methods to modulate gene expression of, for example, genes encoding an ATAP region or ATAP receptor binding protein or a ATAP receptor protein. In particular, the instant invention features nucleic-acid based molecules and methods to modulate the expression of a Bfl-1 protein, HCCS1 protein or ATAP receptor protein.

The description of the various aspects and embodiments herein is provided with reference to the exemplary ATAP nucleic acids provided in the Sequence Listing. However, the various aspects and embodiments are also directed to genes which encode homologs, orthologs, and paralogs of ATAP proteins, ATAP binding proteins, and ATAP receptor genes and include all isoforms, splice variants, and polymorphisms. Those additional genes can be analyzed for target sites using the methods described for ATAP proteins, ATAP binding proteins, and ATAP receptor genes. Thus, the inhibition and the effects of such inhibition of the other genes can be performed as described herein.

By "down-regulate" it is meant that the expression of the gene, or level of RNAs or equivalent RNAs encoding one or more proteins, or activity of one or more proteins, such as ATAP nucleic acids, and ATAP receptor genes, is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of Bfl-1 or HCCS1 using RNA molecules that target the ATAP region, ATAP binding proteins, and ATAP receptor genes with the nucleic acid molecule of the instant invention is greater in the presence of the nucleic acid molecule than in its absence.

By "up-regulate" is meant that the expression of the gene, or level of RNAs or equivalent RNAs encoding one or more protein subunits, or activity of one or more protein subunits, such as ATAP proteins, ATAP binding proteins, and ATAP receptor genes, is greater than that observed in the absence of the nucleic acid molecules of the invention. For example, the expression of a gene, such as ATAP proteins, ATAP binding proteins, and ATAP receptor genes, can be increased in order to treat, prevent, ameliorate, or modulate a pathological condition caused or exacerbated by an absence or low level of gene expression. In one embodiment the invention relates to a method for treating or preventing a hyperproliferative disorder by up-regulating the expression, release, and/or activity of an ATAP protein, ATAP binding proteins, and ATAP receptor genes.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of the nucleic acid molecules of the invention.

By "gene" it is meant a nucleic acid that encodes RNA, for example, nucleic acid sequences including but not limited to a segment encoding a polypeptide.

"Complementarity" refers to the ability of a nucleic acid to form hydrogen bond(s) with another RNA sequence by either traditional Watson-Crick or other non-traditional types.

By "RNA" is meant a molecule comprising at least one ribonucleotide residue. By "ribonucleotide" or "2'-OH" is meant a nucleotide with a hydroxyl group at the 2' position of a D-ribo-furanose moiety.

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

By "nucleic acid molecule" as used herein is meant a molecule having nucleotides. The nucleic acid can be single, double, or multiple stranded and can comprise modified or unmodified nucleotides or non-nucleotides or various mixtures and combinations thereof.

By "equivalent" or "related" RNA to ATAP proteins, ATAP binding proteins, and ATAP receptor genes is meant to include those naturally occurring-RNA molecules having homology (partial or complete) to ATAP-containing proteins, ATAP binding proteins, and ATAP receptor genes encoding for proteins with similar function as ATAP proteins, ATAP binding proteins, and ATAP receptor proteins in various organisms, including human, rodent, primate, rabbit, pig, protozoans, fungi, plants, and other microorganisms and parasites. The equivalent RNA sequence also includes in addition to the coding region, regions such as 5'-untranslated region, 3'-untranslated region, introns, intron-exon junction and the like. By "homology" is meant the nucleotide sequence of two or more nucleic acid molecules is partially or completely identical. In certain embodiments the homolgous nucleic acid has 30%, 40%, 50%, 60%, 70%, 80%, 90%, or 95% homology to an ATAP encoding nucleic acid, for example, SEQ ID NO. 37 or 59; an ATAP binding protein, and/or an ATAP receptor gene.

By "vectors" is meant any nucleic acid-based technique used to deliver a desired nucleic acid, for example, bacterial plasmid, viral nucleic acid, HAC, BAC, and the like.

The nucleic acid molecules of the instant invention, individually, or in combination or in conjunction with other drugs, can be used to treat diseases or conditions discussed above. For example, the subject can be treated, or other appropriate cells can be treated, as is evident to those skilled in the art, individually or in combination with one or more drugs under conditions suitable for the treatment.

As used in herein "cell" is used in its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The nucleic acids of the invention are added directly, or can be complexed with cationic lipids, packaged within liposomes, or otherwise delivered to target cells or tissues. The nucleic acid or nucleic acid complexes can be locally administered to relevant tissues in vitro, ex vivo, or in vivo through injection or infusion pump, with or without their incorporation in biopolymers.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

The nucleic acid molecules of the present invention can be modified extensively to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163).

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Nucleic acid molecules are preferably resistant to nucleases in order to function as effective intracellular therapeutic agents Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

The molecules of the instant invention can be used as pharmaceutical agents. Pharmaceutical agents prevent, inhibit the occurrence, or treat (alleviate a symptom to some extent, preferably all of the symptoms) a disease state in a subject.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose or pharmaceutically effective amount is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl disteacate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The amount of active ingredient that can be combined with the carrier materials to produce a single dosage form varies depending upon the host treated and the particular mode of administration. Dosage unit forms generally contain between from about 1 mg to about 1000 mg of an active ingredient.

It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The composition can also be administered to a subject in combination with other therapeutic compounds to increase the overall therapeutic effect. The use of multiple compounds to treat an indication can increase the beneficial effects while reducing the presence of side effects.

Alternatively, certain of the nucleic acid molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; Dropulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In one aspect the invention features an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

A further object of the present invention is to provide a kit comprising a suitable container, the therapeutic of the invention in a pharmaceutically acceptable form disposed therein, and instructions for its use.

In another embodiment, an isolated nucleic acid molecule of the invention comprises a nucleic acid molecule that is a complement of the nucleotide sequence encoding an ATAP of the invention, an ATAP binding protein, and/or an ATAP receptor. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

As used herein, "fragments" are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

"Derivatives" are compositions formed from the native compounds either directly, by modification, or by partial substitution. "Analogs" are nucleic acid sequences or amino acid sequences that have a structure similar to, but not identical to, the native compound.

Derivatives or analogs of the nucleic acids or proteins of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990).

In yet another embodiment, a nucleic acid of the invention is expressed in mammalian cells using a mammalian expression vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding ATAPs, ATAP binding proteins, and/or ATAP receptors can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG- Tag, fluorescent protein, GST, TAT, an antibody portion, a signal peptide, and the like, at the 5' end, the 3' end, or at any location within the ORF.

In a preferred embodiment, the nucleic acid of the invention comprises a polynucleotide encoding the soluble (i.e., the extracellular) portion of a ATAP receptor. Any of the embodiments described herein, can be achieved using standard molecular biological and genetic approaches well known to those of ordinary skill in the art.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., *Saccharomyces cerevisiae*) or may be a mammalian cell, including a human cell. For long-term, high-yield production of recombinant proteins, stable expression is preferred.

Polypeptides

In other embodiments, the invention pertains to isolated nucleic acid molecules that encode ATAPs, ATAP binding proteins, and/or ATAP receptor polypeptides, antibody polypeptides, or biologically active portions thereof. The polypeptides of the complex can be formed, for example, using a peptide synthesizer according to standard methods; or by expressing each polypeptide separately in a cell or cell extract, then isolating and purifying the polypeptide.

Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of an ATAP, ATAP binding protein, or ATAP receptor protein. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of an ATAP, ATAP binding protein, and/or ATAP receptor protein, variants, portions and/or combinations thereof. In alternative embodiments antibodies of the invention may target and interfere with the ATAP/ATAP receptor interaction to inhibit signaling.

The preparation of monoclonal antibodies is well known in the art; see for example, Harlow et al., Antibodies: A Laboratory Manual, page 726 (Cold Spring Harbor Pub. 1988). Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to ATAP, ATAP binding proteins, and/or ATAP receptor proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352:624-628; Gram et al. (1992) PNAS 89:3576-3580.

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., *Nature* 321: 522, 1986 and Singer et al., *J. Immunol.* 150: 2844, 1993. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., *Nature* 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of an ATAP, an ATAP binding protein, and/or an ATAP receptor that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J. Mol. Biol.* 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology*, 10:779-783 (1992)); Lonberg et al. (*Nature*, 368:856-859 (1994)); Morrison (*Nature*, 368:812-13 (1994)); Fishwild et al, (*Nature Biotechnology*, 14:845-51 (1996)); Neuberger (*Nature Biotechnology*, 14:826 (1996)); and Lonberg and Huszar (*Intern. Rev. Immunol.*, 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., Science 246:1275-1281 (1989)) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i)

an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. Similar procedures are disclosed in WO 93/08829, published May 13, 1993, and Traunecker et al., EMBO J., 10:3655-3659 (1991).

Antibody variable domains with the desired binding specificities (antibody-antigen combining sites) can be fused to immunoglobulin constant domain sequences. For further details of generating bispecific antibodies see, for example, Suresh et al., Methods in Enzymology, 121:210 (1986); and Brennan et al., Science 229:81 (1985).

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The "diabody" technology described by Hollinger et al., Proc. Natl. Acad. Sci. USA 90:6444-6448 (1993) has provided an alternative mechanism for making bispecific antibody fragments. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991). Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HW infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a chemical agent, or a radioactive isotope (i.e., a radioconjugate). Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide-interchange reaction.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight.-Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

Additional objects and advantages of the present invention will be appreciated by one of ordinary skill in the art in light of the current description and examples of the preferred embodiments, and are expressly included within the scope of the present invention.

EXAMPLES

The amphipathic tail-anchor domain is conserved in Bfl1 and HCCS1. The gene encoding Bfl1 (BCL2A1 or BCL2-related protein A1) is located on chromosome 15q24.3 and contains three exons that are transcribed into two alternative splice variants, Bfl1 (175 a.a.) and Bfl1 s (163 a.a.) (Ko et al., 2003b). The tail-anchoring (TA) domain of Bfl1 (a.a. 147-175) is encoded by exon 3. A database search revealed that exon 3 of BCL2A1 is conserved in HCCS1 (16.4 kb) located on 15q25.1 (FIG. 1A). Alignment of the genomic sequences for BCL2A1 and HCCS1 showed that an 8.8 kb fragment of BCL2A1 including exon 3 and the surrounding non-coding regions is highly conserved in HCCS1, possibly as a result of duplication of 12 conserved gene segments.

The genomic sequence of HCCS1 also contains three exons that encode 91 amino acids (FIG. 1A). The DNA sequence for exon 3 of HCCS1 is 95% identical to that for BCL2A1, and both have identical reading frame starting at E28 for HCCS1 and E141 for Bfl1, respectively (FIG. 1B). HCCS1 contains a 28 amino acid stretch (E28 to L55) that is identical to that of the Bfl1 TA, except for a conservative change at L35 (FIG. 1C). A base-pair deletion in HCCS1 at the 3' end of exon 3 leads to a frame shift and subsequent changes in the amino acid sequence at the C-terminus of HCCS1.

Sequence alignments showed a common feature with TA domains of all anti-apoptotic members of the Bcl2 protein family, where a hydrophobic-rich segment (HR) was always surrounded by an N-terminal flanking region (FR-1) and a C terminal flanking region (FR-2) (FIG. 1E). The conserved lysine residues in FR-1 and FR-2 represent potential MTSs for the TA peptide (see below), whereas three charged residues in the HR of Bfl1 (E159, K163 and E166) and HCCS1 (E46, K50 and E53) were unique, since they are not conserved in other Bcl2 family proteins.

Analysis of secondary structures using SOPMA (Geourjon and Deleage, 1995) and Jpred (Cuff et al., 1998) programs predict an α-helical structure for the TA peptide (FIG. 1C). Alignment of amino acids in a α-helical wheel plot revealed the amphipathic nature of the TA peptide from both Bfl1 and HCCS1, with the three charged residues aligning on one side of the α-helix (FIG. 1D). Therefore, we named this domain the amphipathic tail-anchoring peptide (ATAP).

To study the effect of TA on apoptosis, FLAG-TA fusion peptide was transiently expressed in HEK293 cells. 24 h after transfection, cell death was observed by propidium iodide (PI) staining. While FLAG-tagged full-length Bfl-1 (FLAG-Bfl-1) showed no toxic effect on cells, FLAG-TA significantly induced cell death and this toxicity was blocked by 50 μM of OPH, a pan-caspase inhibitor (FIG. 1F). The cytotoxic activity of FLAG-TA was quantified using a β-galactosidase reporter assay (Chittenden et al., 1995; Wood et al., 2000). With co-transfection of plasmids containing either FLAGBfl-1 or Flag-TA along with plasmid containing β-galactosidase gene, the loss of cell viability reflects the decrease in β-galactosidase activity. Transient expression of FLAG-TA resulted in 68.1±3.9% (n=5) decrease in β-galactosidase activity, which was inhibited by 50 μM OPH (FIG. 1G). Interestingly, expression of FLAG-Bcl-xL or FLAG-Bfl-1 leads to increased β-galactosidase activity (1.32±0.13 fold over control for FLAG-Bcl-xL (n=5); and 1.11±0.06 for FLAG-Bfl-1 (n=5)), likely correspond to the prosurvival activity of Bcl-xL and Bfl-1. The expression levels of FLAG-tagged proteins correlated with their β-galactosidase activities (FIG. 1H). Notably, the expression FLAG-TA was increased by treatment with 50 μM of OPH, suggesting that TA peptide is targeted for proteolytic degradation in cells undergoing apoptosis, or the death of cells associated with expression of TA.

ATAP induces apoptosis independent of Bax and Bak. To test the cellular function of ATAP, a Flag-ATAP fusion peptide was transiently expressed in HEK293 cells to allow for detection of the recombinant protein using anti-Flag antibody (FIG. 2A). Twenty-four hours after transfection, the cytotoxic activity of Flag-ATAP was quantified using a β-galactosidase reporter assay (Chittenden et al., 1995; Wood and Newcomb, 2000). With co-transfection of plasmids containing β-galactosidase gene and Flag-ATAP cDNA, the decrease in β-galactosidase activity reflects the loss of cell viability. Compared with cells co-transfected with the mock plasmid, a 68.1±3.9% (n=5) decrease in β-galactosidase activity was observed in cells transfected with Flag-ATAP, which could be prevented by the addition of 50 μM OPH, a pan-caspase inhibitor (FIG. 2A). Moreover, elevated expression of Flag-ATAP was observed in cells treated with OPH, suggesting that either ATAP is a potent trigger of cell death or the peptide is targeted for proteolytic degradation in cells undergoing apoptosis.

We assembled a GFP-ATAP fusion construct to allow live cell imaging of ATAP-induced cell death. As shown in FIG. 2B, cells transiently expressing GFP-ATAP displayed a condensed and fragmented chromatin structure, illustrating the apoptotic nature of cell death. The GFP-ATAP-induced chromatin fragmentation could be prevented with the addition of OPH. Quantitative analysis of GFP-ATAP-induced apoptosis in HEK293 cells was performed using FACS assays, where elevation of the sub-G1 cell population was used as an index for cells undergoing apoptosis (FIG. 2C). Clearly, the pro-apoptotic activity of GFP-ATAP is similar to, or perhaps stronger than, that of GFP-Bax, a well-known pro-apoptotic protein (Pan et al., 2001; Smaili et al., 2001) (FIG. 2C). As a control, we found that expression of GFP-TAxL, containing the Bcl-xL TA domain (a.a. 202-233) attached to the C terminus of GFP, did not show any toxic activity in HEK293 cells.

To test whether there were any cell-type dependent effects of ATAP, GFP-ATAP was transiently expressed in cell lines with different genetic backgrounds. In addition to HEK293 and HeLa cells, we tested GFP-ATAP in MCF-7, a caspase-3 deficient human breast cancer cell line (Janicke et al., 1998), and BMK-D3, a baby mouse kidney cell line derived from bax−/−bak−/− mice (Degenhardt et al., 2002). Cell death analyses using the propidium iodide (PI) exclusion method revealed that >90% of all cell types underwent apoptosis after transient expression of GFP-ATAP (FIG. 2D,E). Since pronounced apoptosis is observed in BMK-D3 cells that lack Bax and Bak (FIG. 2E and supplementary material FIG. S2), the proapoptotic activity of GFP-ATAP does not require the participation of Bax and Bak. Moreover, the strong proapoptotic effect of GFP-ATAP on MCF-7 cells suggests that ATAP can act through caspases other than caspase-3.

The amphipathic nature of ATAP is essential for its proapoptotic activity. Since the charged residues in the HR of Bfl1 and HCCS1 are not present in other Bcl2 family proteins, and since they contribute to the amphipathic nature of ATAP, we tested the contribution of E159, K163 and E166 to the pro-apoptotic function of ATAP in Bfl1 through site-directed mutagenesis. To allow the determination of subcellular localization, the various ATAP mutants were fused with GFP (FIG. 3A). While mutation of a single residue has little effect on the apoptotic activity of ATAP, double mutations, e.g. E159Q-E166Q (mHR3) or E159L-E166L (mHR4), markedly reduce the proapoptotic function of ATAP (FIG. 3B). An additional mutation (K163L) in mHR3 further decreased toxicity of ATAP in mHR7. Interestingly, the mHR5 construct containing the E159K-E166K mutation did not appear to affect the proapoptotic activity of ATAP (FIG. 3B), suggesting that conservation of charge rather than the polarity of the charge is involved in its pro-apoptotic function. Using the β-galactosidase reporter assay, we found that Flag-mHR3, in which the GFP sequence is replaced with the Flag sequence, also displayed significantly reduced cytotoxic effect compared with the Flag-ATAP construct. Twenty-four hours after transfection, β-galactosidase activity was 26.0±5.2% in Flag-ATAP-transfected cells, whereas it was 62.0±7.8% in FlagmHR3-transfected cells (n=5, P<0.001) (FIG. 3C), compared with enzyme activity from GFP-transfected cells.

To test whether the amphipathic nature of ATAP is also involved in the apoptotic function of HCCS1, corresponding mutations of charged residues were introduced into the full length HCCS1 gene. As shown in FIG. 3D, HCCS1-GFP (E46Q/E53Q) containing mutations corresponding to mHR3 of the Bfl1 ATAP exhibited significantly reduced cytotoxic activity. In further studies, we also tested the effect of ATAP and mHR7 in BMK-D3 cells lacking the expression of Bak and Bax, and in CHO cells stably transfected with Bcl-xL (Pan et al., 2000) (see supplementary material FIG. S2). A similar cytotoxic effect of ATAP was observed in parental CHO cells compared with CHO cells overexpressing Bcl-xL, and in BMK-wt cells compared with BMK-D3 cells, suggesting that the pro-apoptotic function of ATAP is independent of Bax, Bak and Bcl-xL. Moreover, although GFP-ATAP showed potent cytotoxic effects on both CHO and BMK cell lines, GFPmHR7 showed little cytotoxicity. Taken together, these results demonstrate that the pro-apoptotic activity of ATAP is closely related to the amphipathic property of the peptide.

Figure 4:
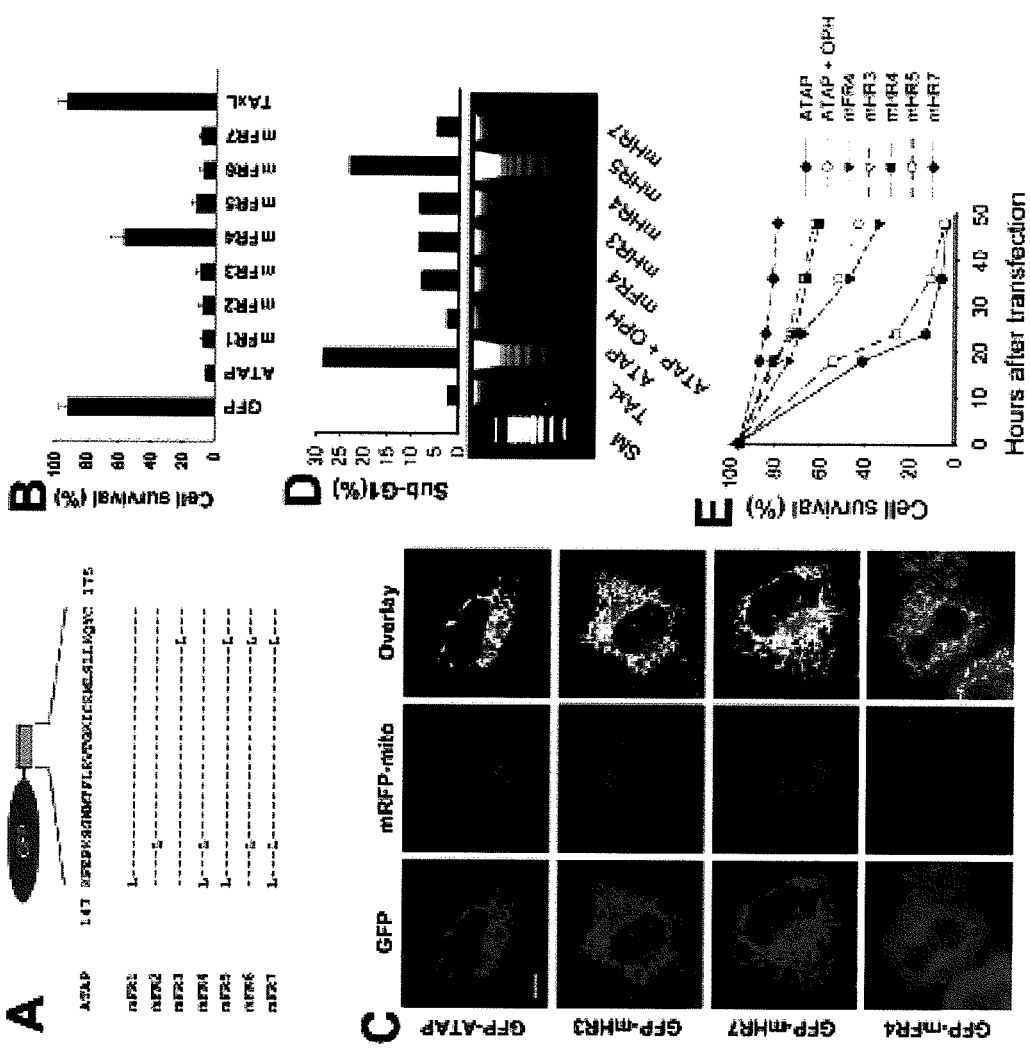
FIG. 4. The pro-apoptotic activity of ATAP involves targeting to mitochondria. (A) Schematic representation of the GFP-ATAP constructs (See SEQ ID NOs. 38-44) in which point mutations were introduced into the flanking regions of the ATAP. (B) Cell survival was measured by PI exclusion in the HEK293 cells transfected with 1 μg GFP-ATAP mutant constructs 24 hours after transfection. (C) Subcellular localization of ATAP mutants fused with GFP. HeLa cells were transfected with 0.5 μg of the indicated plasmids. Cell culture was performed in the presence of 50 μM OPH to prevent rapid cell death. 18 hours after transfection, cells were incubated in medium containing 50 nM MitoTracker for 2 hours and fixed using 4% paraformaldehyde. Localization of GFP fusion proteins was observed using confocal microscopy. Bar, 10 μm. (D) Cellular effects of GFPATAP mutants on apoptosis. HEK293 cells were transiently transfected with the indicated plasmids expressing ATAP mutants fused with GFP. 18 hours after transfection, cells were harvested, fixed, and stained with PI. The DNA content of GFP-positive cells was then analyzed by flow cytometry (upper panel). DNA fragmentation was also analyzed by electrophoresis on 2% agarose gels (lower panel). SM, 100 bp ladder size marker. (E) Time-course effect of GFP-ATAP and GFP-ATAP mutants on HEK293 cells. Cell survival was measured by PI exclusion in the HEK293 cells transfected with 1 μg GFP-ATAP mutant constructs.

ATAP targets mitochondria permeability transition to induce apoptosis Confocal microscopic imaging showed that mutations at E159, E166 or K163 of ATAP did not alter its intracellular targeting properties. Indeed, all mHR1 to mHR7 mutants are localized to the mitochondrial membrane, similarly to the wild-type GFP-ATAP, based on co-localization pattern with mRFP-Mito transiently expressed in HeLa cells (FIG. 4C). Previous studies from other investigators have shown that positively charged residues located at the N-terminus or C-terminus of the TA domain are involved in targeting of the TA peptide to mitochondria (Borgese et al., 2003; Kaufmann et al., 2003). We found that the conserved lysine residues located in FR-1 and FR-2 played a critical role in targeting of ATAP to the mitochondria membrane (FIG. 4). Although mutation of single lysine residues, K147L, K151L or K172L, did not appear to alter the mitochondrial-targeting property of ATAP, double mutation of K147L-K151L (mFR4) caused mistargeting of GFP-ATAP away from the mitochondria (FIG. 4C). The mFR4 mutant localized mainly to the cytoplasm and often formed cytosolic or perinuclear aggregates, with remarkably reduced pro-apoptotic activity compared with the other mFR constructs (FIG. 4B).

In cells undergoing apoptosis, the degradation of chromosomal DNA can be measured in the sub-G1 population of cells containing lower DNA content than healthy cells, or can be detected as a DNA ladder of about 180 bp on an agarose gel. As shown in FIG. 4D, HEK293 cells expressing GFP-ATAP and mHR5 displayed a significantly higher percentage of sub-G1 cells with a more extensive DNA laddering pattern than those expressing mFR4, mHR3, mHR4 or mHR7, confirming the apoptotic nature of cell death induced by ATAP. The timedependent effects of the various ATAP mutants on apoptosis were further assayed using the PI exclusion method (FIG. 4E). Forty-eight hours after transfection of HEK293 cells with either ATAP or mHR5, more than 95% of cells were PI positive, whereas only about 38% of cells were PI positive with expression of either mHR3 or mHR4. In the case of mHR7-transfected cells, only 19% cells were PI positive at the 48-hour time point (FIG. 4E). Interestingly, cells transfected with mFR4 exhibited progressive cell death at later stages of the experiment (e.g. more than 36 hours after transfection). Although the mitochondrial targeting of mFR4 seemed to be impaired, a portion of the protein was detected at the mitochondria (FIG. 4C). One possibility is that the delayed toxic effect of mFR4 results from the gradual accumulation of the molecule at the mitochondrial membrane.

One particular exception is found with the mFR7 mutant, where all three lysine residues in FR-1 and FR-2 were mutated to leucines. Unlike mFR4, mFR7 still maintained its targeting to mitochondria and possessed a potent pro-apoptotic activity (FIG. 4B). Analysis of the primary amino acid sequence of GFP-mFR7 identified other charged residues from the Cterminal portion of GFP and the multiple cloning site (MCS) of the pEGFP-C1 plasmid that resides proximal to the ATAP sequence. This external sequence resembles the FR-1 region of Bcl-xL in terms of charge contents and positioning, which could act as surrogate for the MTS in the absence of positively charged residues within the Bfl1 flanking regions (see supplementary material FIG. S3). Indeed, deletion of these positively charged residues eliminated the mitochondrial targeting of mFR7 and consequently its pro-apoptotic function. Moreover, insertion of an 11 amino acid linker sequence into the MCS also eliminated mitochondrial targeting of mFR7 and reduced its apoptotic activity. These results are consistent with previous studies of Kaufmann et al. (Kaufmann et al., 2003) Journal of Cell Science 120 (16) and further suggest that charged residues must remain adjacent to HR segment for efficient targeting of ATAP to MOM.

Overall, our data suggest that lysine residues located in the N-terminal flanking regions of ATAP are essential for targeting of ATAP to mitochondria, and that the pro-apoptotic activity of ATAP is closely linked to its association with mitochondria.

Both the MTS and ATAP are involved apoptosis induced by HCCS1. The primary amino acid structure of HCCS1 contains a stretch of 18 amino acids (a.a. 1-18) that are proximal to the ATAP sequence, and may act as an alternative MTS for HCCS1 (see FIG. 1C). To explore the contribution of MTS and ATAP to the apoptotic function of HCCS1, we generated GFP fusion constructs with various HCCS1 deletion mutants (FIG. 5A). Due to the high level of toxicity produced by ATAP, it was necessary to include 50 µM OPH in the cell culture medium in experiments where we visualize the mitochondrial localization patterns of the various GFP fusion constructs.

As shown in FIG. 5B, HCCS1-GFP, as well as GFP-ATAP (HCCS1), exhibited close co-localization with mRFP-Mito in HeLa cells, demonstrating the specific targeting of HCCS1 at the mitochondria membrane. Attachment of GFP to the Nterminus of HCCS1 lacking MTS, GFP-HCCS1 (ΔMTS), also revealed a characteristic mitochondria localization pattern, confirming our observation that the ATAP domain of HCCS1 contained an intrinsic MTS. Interestingly, attachment of GFP to the C-terminus of HCCS1 lacking MTS caused mistargeting of HCCS1 (ΔMTS)-GFP away from the mitochondria. This is consistent with earlier studies demonstrating that addition of a large moiety to the C terminal end of TA proteins disrupted their intracellular targeting properties (Johnston et al., 2002).

The MTS-GFP also exhibited a typical mitochondrial localization pattern, indicating that the MTS domain of HCCS1 possesses mitochondrial-targeting properties (FIG. 5B). Therefore, HCCS1 contains dual targeting signals for mitochondrial localization, one at the N-terminus (MTS) and one at the C-terminus (ATAP). Cell viability analyses using the PI exclusion method showed that MTS-GFP had no toxic effect in HeLa cells, whereas HCCS1-GFP, GFP-HCCS1 (ΔMTS) and GFP-ATAP (HCCS1) all exhibited potent proapoptotic activities that could be inhibited by OPH. Moreover, HCCS1 (ΔMTS)-GFP, which mistargets from mitochondria, displayed significantly lower cytotoxicity (FIG. 3C). These results further support the notion that ATAP is responsible for the pro-apoptotic activity of HCCS1 and that mitochondrial targeting is required for the pro-apoptotic function of HCCS1.

Figure 6:
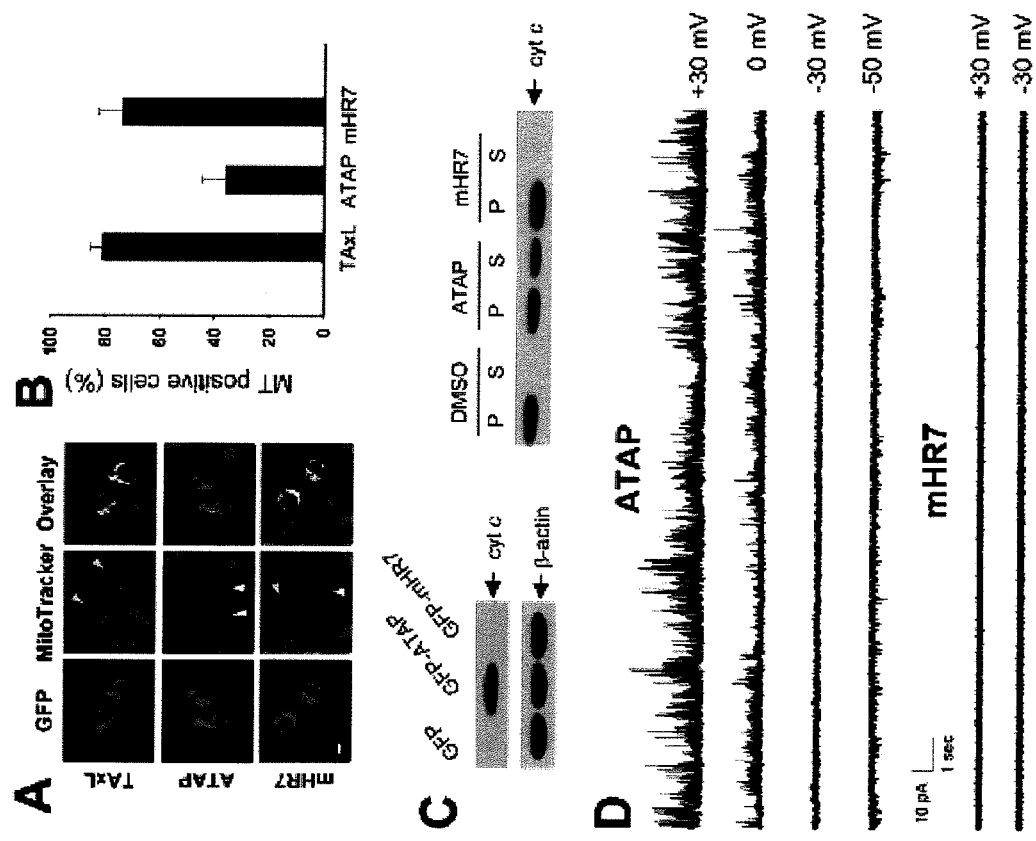
FIG. 6. ATAP induces the loss of mitochondrial membrane potential and perturbs membrane permeability in planar lipid bilayers. (A) Effect of GFP-ATAP on the mitochondrial membrane potential. Mitochondrial outer membrane potential was observed using MitoTracker Red (CM-H2 TMRos) dye. HeLa cells were transfected with GFP-ATAP, GFP-mHR7 or GFP-TAxL and cultured in the presence of 50 µM OPH. 24 hours after transfection, cells were incubated in medium containing 50 nM of MitoTracker for 2 hours and observed under a fluorescence microscope. Bar, 10 µm. (B) Green (GFP) and red (MitoTracker) double-positive cells were quantified from about 300 GFP positive cells from three different fields. Data are expressed as the mean±s.e. (C) Effect of ATAP on cytochrome c release. Left panel, HEK293 cells were transfected with 1 µg of pEGFP (lane 1), pEGFP-ATAP (lane 2) or pEGFPmHR7 (lane 3). 20 µg mitochondria free cytosol proteins were analyzed by western blotting using anti-cytochrome c antibody. Right panel, mitochondria membrane isolated from BMK-D3 cells were incubated with synthetic ATAP and mHR7 peptides (100 µM). ATAP induced cytochrome c release into the supernatant (S), whereas cytochrome c remained in the pellet (P) in preparations treated with mHR7 and DMSO (as a control). (D) Effect of synthetic ATAP and mHR7 peptides on the membrane permeability of planar lipid bilayer. The peptides (11.1 µM) were added to the cis chamber. Current traces at the corresponding holding potentials were measured from recording solution of 200 mM KCl (cis) and 50 mM NaCl (trans). Data are representative of n=5 for ATAP and n>35 for mHR7.

ATAP perturbs membrane permeability in lipid bilayer assay. Extensive studies have shown that loss of mitochondrial membrane potential acts as a trigger for cytochrome c release and caspase activation in apoptosis signaling (Petit et al., 1995; Zamzami et al., 1995). To determine whether the loss of mitochondrial membrane potential is directly involved in ATAP-induced apoptosis, we monitored mitochondrial membrane potential in HeLa cells using MitoTracker Red (CM-H2 TMRos), which targets mitochondria and develops fluorescence by oxidation, only in cells with intact mitochondrial membrane potential. HeLa cells were transfected with GFP-ATAP, GFP-mHR7 or GFP-TAxL, in the presence of 50 µM OPH to reduce the downstream effect of caspase activation on mitochondrial integrity. Although most of cells transfected with GFP-TAxL were healthy with bright MitoTracker staining, a majority of the GFP-ATAP transfected cells showed diffuse and low intensity MitoTracker staining (FIG. 6A). On average, 65.0±8.7% (n=5) of HeLa cells expressing GFP-ATAP were MitoTracker negative, whereas only 19.0±9.3% of those expressing GFP-TAxL were MitoTracker negative (FIG. 6B). However, cells transfected with GFP-mHR7 showed increased MitoTracker staining that was comparable that in cells transfected with GFP-TAxL. Similar results were obtained with the other mHR and mFR Journal of Cell Science 120 (16) mutant constructs, where development of MitoTracker labeling is closely associated with the reduced toxic effects of the ATAP constructs (not shown). These results indicate that ATAPinduced apoptosis could involve the direct induction of mitochondria outer membrane permeabilization.

Using the lipid bilayer reconstitution system, we demonstrated that the synthetic wild-type ATAP peptide produced significant effects to the cation permeability of the lipid bilayer membrane, whereas a mutant mHR7 peptide, which can bind to the mitochondria membrane but is not toxic to the cells, did not affect conductance of the lipid bilayer membrane. The ATAP-mediated permeability changes in the in vitro system did not display the typical stable conductance behavior one would expect from a pore-forming channel. ATAP could either interact with or modulate the pre-existing channels to alter mitochondrial membrane permeability, or potentially other domains of the Bfl1 or HCCS1 proteins may contribute to changes in membrane permeability observed in vivo.

Cytochrome c release is a critical step in the initiation of the mitochondrial apoptosis pathway. To test the effect of ATAP and mHR7 on cytochrome c release from mitochondria, we performed two complementary assays. First, using transient expression of GFP-ATAP in HEK293 cells, we found that a significant portion of cytochrome c is released into the cytosol in cells transfected with GFP-ATAP, whereas GFP-mHR7 does not produce significant cytochrome c release (FIG. 6C, left). Second, using isolated mitochondria membrane preparations from BMK-D3 cells, we found that addition of synthetic ATAP peptide induced release of cytochrome c—an effect that was not observed with mHR7 peptide (FIG. 6C, right).

As a direct test of the effects of ATAP on the integrity of cellular membranes, we performed electrophysiological studies using the lipid bilayer reconstitution system (Lam et al., 1998; Ma et al., 1988). The toxic effect of ATAP in E. coli (not shown) prevents purification of the peptide in sufficient quantity for our functional studies. Therefore, synthetic ATAP peptides were used in our bilayer reconstitution assays. As shown in FIG. 6D, addition of the wild-type ATAP peptide (11 µM) produced a significant effect on the permeability of the lipid bilayer membrane to monovalent cations. In a recording solution containing 200 mM KCl (cis) and 50 mM NaCl (trans), outward current from cis to trans was measured at 0 mV holding potential, suggesting that ATAP influences the cation permeability of the lipid bilayer membrane (n=5). Although the current traces fluctuate at variable levels without a definable unitary conductance, a clear reversal potential for currents was measured at ~−30 mV, which is close to the Nernst potential for cations. ATAP at higher concentrations (>22.2 µM) often caused instability of the bilayer membrane, with rupture of the lipid bilayer occurring within 30 minutes of addition of the peptide (n>30). Thus, high concentrations of ATAP could affect the permeability of the lipid bilayer membrane, without forming a stable pore structure. In parallel experiments, we found that the mHR7 mutant peptide did not induce any notable changes in membrane conductance, at concentrations of 11-44 µM (n=35, FIG. 6D). This result is consistent with the reduced apoptotic activity of the mHR7 protein transiently expressed in cells.

Examplary Methods.

Assessment of Mitochondrial Membrane Potential and Confocal Microscopy.

Mitochondrial membrane potential was measured following the protocol of Pratt and Niu (2003). Transiently transfected Hela cells were incubated for 2 hr in medium containing 50 nM MitoTracker Red CM-H2Xros (Molecular Probes), which develops fluorescence only in cells with an intact mitochondrial membrane potential. Living cells were observed and photographed on a fluorescence microscope. MitoTraker-positive cells were counted from at least 200 GFP-positive cells. To observe intracellular localization of EGFP fusion proteins, fixed Hela cells were used for confocal microscopy. Hela cells were transfected as described above on LabTek II chamber slides and cultured in the presence of 50 nM OPH. 18 h after transfection, cells were stained with 50 nM MitoTracker Red CM-H2Xros and washed with PBS followed by fixation with 4% formaldehyde. Cells finally were washed, mounted and analyzed with a confocal microscope Zeiss LSM 510 (Carl Zeiss Microscopy, Jena, Germany) equipped with a 63× objective. Image acquisition was performed at the room temperature.

Plasmid Construction

PCR-based mutagenesis and subcloning were used to construct all plasmids used in this study (Ko and Ma, 2005). Primer sequences used for subcloning and mutagenesis are listed. PCR product encoding ATAP was amplified using pBfl1-myc (Ko et al., 2003b) as a template, and that encoding the TA of Bcl-xL (E202-K233) was amplified using pEGFP-BclxL plasmid (Ko et al., 2003a) as a template. The PCR products were cloned inframe behind the GFP sequence into XhoI and EcoRI sites in pEGFP-C1 (Clontech), to obtain the pGFP-ATAP and pGFP-TAxL plasmids. MGC clone 584619 containing the full-length cDNA of HCCS1 was purchased from ATCC, and used as a PCR template to construct pHCCS1-GFP, pHCCS1 (_MTS)-GFP, pMTS-GFP, pGFP-HCCS1 (_MTS) and pGFP-ATAP (HCCS1). The plasmids with GFP fused to the 3_ end were generated through subcloning of PCR products into the BspE1 and EcoRI sites of pEGFP-N1 (Clontech) vector. To generate pFLAG-ATAP and pFLAG-mHR3, cDNA fragment encoding GFP of pGFP-TA and pGFP-mHR3 plasmids was replaced by cDNA fragment coding the Flag epitope. We used the following oligos containing 3_ ends of 23 bases complementary (italics) between sense and antisense primers (bold italic). The two overlapping oligos were annealed and subcloned into the XhoI and EcoRI sites (bold) of pGFP-ATAP and pGFPmHR3.

For construction of the Bfl-1 FR mutants (See text), various combinations of the following primers were used in PCR reaction using pBfl-1-myc as a template.

| Primer | Sequence (5' to 3') |
|---|---|
| TA-F (SEQ ID NO. 10) | AACTCGAGCTAAGTTTGAACCTAAATCTGGCTGG |
| TA-R (SEQ ID NO. 11) | TTGAATTCAACAGTATTGCTTCAGGAGAGATAG |
| K1L-F (SEQ ID NO. 12) | AACTCGAGCTCTGTTTGAACCTAAATCTGGCTGG |
| K5L-F (SEQ ID NO. 13) | AA-CTCGAGCTAAGTTTGAACCTCTATCTGGCTGGATGACTTTT |
| K1,5L-F (SEQ ID NO. 14) | AACTCGAGCTCTGTTTGAACCTCTATCTGGCTGGATGACTTTT |
| K26L-R (SEQ ID NO. 15) | TTGAATTCAACAGTATTGCAGCAGGAGAGATAGCATTTCAC |

For construction of the Bfl-1 FR mutants (See text), various combinations of the following primers were used in PCR reaction using pBfl-1-myc as a template.

The combinations of primers used for PCR reaction were K1L-F and TA-R for mFR1; K5L-F and TA-R for mFR2, TA-F and K26L-R for mFR3, K1,5L-F and TA-R for mFR4; K1L-F and K26L-R for mFR5; K5L-F and K26L-R for mFR6; K1,5L-F and K26L-R for mFR7 mutant. Restriction sites XhoI and EcoRI (bold) were used for subcloning of PCR products containing mutant codon (underlined) into pEGFP-C1.

For construction of the Bfl-1 TMS mutants (See text) and pEGFP-TAxL (202-239 amino acids of Bcl-xL C-terminal), various combinations of the following synthetic oligos were used.

| Primer | Sequence (5' to 3') |
|---|---|
| sTA-F (SEQ ID NO. 16) | ACTCGAGCTAAGTTTGAACCTAAATCTGGCTGGATGACTTTTCTAGAAGTTACAGGAAAGATCTGT |
| sTA-R (SEQ ID NO. 17) | TTGAATTCAACAGTATTGCTTCAGGAGAGATAGCATTTCACAGATCTTTCCTGTAACTT |
| E13Q-F (SEQ ID NO. 18) | ACTCGAGCTAAGTTTGAACCTAAATCTGGCTGGATGACTTTTCTACAAGTTACAGGAAAGATCTGT |
| E20Q-R (SEQ ID NO. 19) | TTGAATTCAACAGTATTGCTTCAGGAGAGATAGCATTTGACAGATCTTTCCTGTAACTT |
| E13L-F (SEQ ID NO. 20) | AACTCGAGCTAAGTTTGAACCTAAATCTGGCTGGATGACTTTTCTACTAGTTACAGGAAAGATCTGT |
| E20L-R (SEQ ID NO. 21) | TTGAATTCAACAGTATTGCTTCAGGAGAGATAGCATTAGACAGATCTTTCCTGTAACTT |
| E13K-F (SEQ ID NO. 22) | AACTCGAGCTAAGTTTGAACCTAAATCTGGCTGGATGACTTTTCTAAAGGTTACAGGAAAGATCTGT |
| E20K-R (SEQ ID NO. 23) | TTGAATTCAACAGTATTGCTTCAGGAGAGATAGCATCTTACAGATCTTTCCTGTAACTT |
| K17L-F (SEQ ID NO. 24) | AACTCGAGCTAAGTTTGAACCTAAATCTGGCTGGATGACTTTTCTAGAAGTTACAGGACTAATCTGT |
| K17L-R (SEQ ID NO. 25) | TTGAATTCAACAGTATTGCTTCAGGAGAGATAGCATTTCACAGATTAGTCCTGTAACTT |
| KE2L-F (SEQ ID NO. 26) | AACTCGAGCTAAGTTTGAACCTAAATCTGGCTGGATGACTTTTCTACAAGTTACAGGACTAATCTGT |
| KE2L-R (SEQ ID NO. 27) | TTGAATTCAACAGTATTGCTTCAGGAGAGATAGCATTTGACAGATTAGTCCTGTAACTT |
| TAxL-F (SEQ ID NO. 28) | AACTCGAGCTGAGAGCCGAAAGGGCCAGGAACGCTTCAACCGCTGGTTCCTGACGGGCATGACTGTGGCCGGCGTGGTT |
| TAxL-R (SEQ ID NO. 29) | TTGAATTCATTTCCGACTGAAGAGTGAGCCCAGCAGAACCACGCCGGCCACAGT |

The oligos contained 3' ends of 18 bases complementary between sense and antisense primers (bold Italic). The combinations of oligos were E13Q-F and sTA-R for mHR1; sTA-F and E20Q-R for mHR2; E13Q-F and E20Q-R for mHR3; E13L-F and E20L-R for mHR4; E13K-F and E20K-R for mHR5; K17L-F and K17L-R for mHR6; and KE2L-F and KE2L-R for mHR7 mutant. TAxL-F and TAxL-R were used for TAxL construct. The two overlapping oligos were annealed, filled up and then subcloned into the XhoI and EcoRI sites of pEGFP-C1.

To generate pEGFP-TAΔFR-1, the following synthetic oligos were annealed and subcloned into the XhoI and EcoRI sites of pEGFP-C1.

| Primer | Sequence (5' to 3') |
| --- | --- |
| TAΔFR-1F (SEQ ID NO. 30) | TCGAGGCTGGATGACTTTTCTAGAAGTTACAG GAAAGATCTGTGAAATGCTATCTCTCCTGAA GCAATG |
| TAΔFR-1R (SEQ ID NO. 31) | AATTCATTGCTTCAGGAGAGATAGCATTTCACA GATCTTTCCTGTAACTTCTAGAAAAGTCATCC AGCC |

To generate pGFP-linker-ATAP and pGFP-linker-ATAP, mutants including pGFP-linker-mFR7 were generated by substitution of cDNA sequences in pGFPATAP and ATAP mutant plasmids with synthetic cDNA fragments encoding GLPAQITFLSVPGSR.

The following synthetic oligos were annealed and subcloned into the BspEI and XhoI sites of pGFP-ATAP and ATAP mutant constructs:

| Primer | Sequence (5' to 3') |
| --- | --- |
| Linker-F (SEQ ID NO. 32) | CCGGACTCCCCGCCCAGATCACCTTCCTGAGC GTGCCCGGCTC |
| Linker-R (SEQ ID NO. 33) | TCGAGAGCCGGGCACGCTCAGGAAGGTGATCTG GGCGGGGAGT |

To generate pFLAG-TA and pFLAG-mHR3, cDNA fragment encoding EGFP of pEGFPTA and pEGFP-mHR3 plasmids were replaced by cDNA fragment coding FLAG epitope. We used two following oligos containing 3' ends of 23 bases complementary between sense and antisense primers (bold Italic). The two overlapping oligos were annealed, filled up and then subcloned into the XhoI and EcoRI sites of pEGFP-TA and pEGFPmHR3.

To construct expression vector mRFP-mito, mRFP (monomeric red fluorescence protein) cDNA fragment was amplified using pRSETB-mRFP (Campbell et al., 2002) as a template. The PCR product was subcloned into NheI and BspEI sites of pGFP-TAxL to replace GFP by mRFP and generate pmRFP-mito. All constructs were verified by DNA sequencing.

| Primer | Sequence (5' to 3') |
| --- | --- |
| FLAG/FP4-F (SEQ ID NO. 34) | CCGCTAGCGCTACCGGTCGCCACCATGGACTA CAAAGACGATGACGACAAGCTTGAA TTCGATTTTCCACCTCCC |
| FLAG/FP4-R (SEQ ID NO. 35) | AGCTCGAGATCTGAGTCCGGACTTGTAGCTGCC CAGTTCTTCATCGGTAGGGGGAGGTG GAAAATCGAATTCAA | pHCCS-1-GFP (E46Q/E53Q) was obtained by mutagenesis using BsmBI as described (Ko and Ma, 2005). PCR amplification was performed using pHCCS-1-GFP as a PCR template and the following primers:

| Primer | Sequence (5' to 3') |
| --- | --- |
| HCCS-mF (SEQ ID NO. 55) | AACGTCTCAAGGAAAGATCTGTCAGATGCTCTTC TGTCCTGAAGCAATA |
| HCCS-mR (SEQ ID NO. 56) | AACGTCTCATCCTGTAACCTGTAGAAAAGTCATC CAGCCAGATTTA |
| HCCS-anchor-F (SEQ ID NO. 57) | AATCCGGAATGAGAGTTTCATTCTGTCGCCCAGG |
| HCCS-anchor-R (SEQ ID NO. 58) | AAGAATTCAAAAGTAGAAGTATGTGTTGGCAA TCG |

The mutant cDNA fragment of HCCS-1 was subcloned into BspEI and EcoRI sites of the pEGFP-N1 vector.

Bioinformatic Analyses

Genomic sequences of human Bfl1 (GeneID 597) and HCCS1 (GeneID 400410) were obtained from GenBank database and homology searches were carried out using the BLAST program. The genomic locations containing BCL2A1(Bfl1) and HCCS1 are NM_004049 on chromosome 15q24.3 region from 78,040 to 78,050 kb, and XM_375224 on chromosome 15q25.1 region from 77,978 to 77,994 kb, respectively. Alignment of the genomic sequences of BCL2A1 and HCCS1 was performed with the AVID program using a window size of 100 bp. Alignment of exon sequences and primary amino acid sequences were carried out with the CLUSTALW program. Secondary structure was predicted using SOPMA (Geourjon and Deleage, 1995) and Jpred (Cuff et al., 1998) programs. The MTS of HCCS1 was inferred using Targetp v1.1 (Emanuelsson et al., 2000; Nielsen et al., 1997).

mRNA expression of Bfl1 and HCCS1 in normal human tissues and cancer cell lines. Initial analysis with distribution of BCL2A1 and HCCS1 transcripts in normal human tissues was performed using the available microarray data and EST expression profiles provided by NCBI UniGene server. Semi-quantitative evaluation of BCL2A1 and HCCS1 transcripts was analyzed by RT-PCR, using total RNA of human normal lung, breast and cervix were purchased from Stratagene (La Jolla, Calif.). Total RNA of cancer cell lines was isolated using Tri-reagent (Sigma), according to the manufacturer's instructions. 1 µg RNA was used in a 20 µl cDNA synthesis reaction using oligo (dT)18 primer and Moloney murine leukemia virus (MMLV) reverse transcriptase (Promega, Madison, Wis., USA). cDNA mixture (2 µl) was used for PCR amplification. As a control, human α-actin cDNA was amplified to determine the integrity of the RNA and the efficiency of the cDNA synthesis. The primers were 5'-ACAAAATGTTGCGTTCTCAGTCCA-3' (sense) (SEQ ID NO: 60) and 5'-CGTTTTGCCTTATCCATTCTCC-3' (SEQ ID NO: 61) 2922 Journal of Cell Science 120 (16) (anti-sense) for Bfl1; 5'-TTGCCACAAATGGTGT-GCTCTA-3' (sense) (SEQ ID NO: 62) and 5'-TCCTGGT-GCCATGATTTACTGT-3' (SEQ ID NO: 63) for HCCS1; 5'-GATCAGCAAGCAGGAGTATGAC-3' (sense) (SEQ ID NO: 64) and 5'-ATGGCAAGGGACTTCCTGTAAC-3' (antisense) (SEQ ID NO: 65) for α-actin. These primers amplified the 302, 320 and 352 bp PCR products of Bfl1, HCCS1 and α-actin, respectively.

Gene Transfection and Analysis of Cell Death.

Apoptotic cell death was monitored after transfection of expression plasmids into HEK293, HeLa, MCF-7 or BMK D3 cells. $2\times10^5$ cells were cultured in 35-mm wells for 24 hours in Dulbecco's modified Eagle's medium (DMEM) supplemented with 10% fetal bovine serum. Cells were transfected using the Lipofectamine 2000 reagent (Invitrogen), with 1 µg of the indicated expression plasmids and further cultured in the absence or presence of 50 µM of pan-caspase inhibitor, Q-VD-OPH (OPH, Enzyme Systems Products). For morphological assessment of apoptotic cell death, cells were plated onto LabTek II chamber slides (Nalgen Nunc International) at densities of $5\times10^4$ cells per well. 24 hours after transfection, cells were washed with phosphate-buffered saline (PBS) prior to fixation with 4% formaldehyde. Subsequently, cells were stained with a Vectasheild mounting solution (Vector Laboratories) containing 1 µg/ml of DAPI and visualized under an Axiovert 100 inverted epifluorescence microscope (Carl Zeiss). Nuclei with rippled contours and chromatin condensation were considered to represent the apoptotic cell death. Cell death was also measured by propidium iodide (PI) exclusion. After transfection with GFP fusion plasmids, a total of 1 µg/ml PI (Molecular Probes) was added to the cell culture medium. Cells were observed and photographed with a fluorescence microscope at three different fields containing approximately 200 GFP-positive cells. GFP and PI double-positive cells were counted as dead cells. Quantitative analysis of cell viability was determined by _-galactosidase reporter assay according to the procedures as described (Chittenden et al., 1995; Wood and Newcomb, 2000). Briefly, cells were co-transfected with 1 µg of tested plasmid plus 0.1 µg of pCMVβ (Sigma) plasmid expressing β-galactosidase. At 24 hours following transfection, cells were harvested and β-galactosidase activity was measured using β-Galactosidase Enzyme Assay System (Promega). In every experiment, each construct was tested in triplicate, and experiments were repeated at least three times. Cell viability is shown as the relative β-galactosidase activity to the control plasmid.

DNA Fragmentation Assay and Flow Cytometry

To analyze DNA fragmentation by agarose gel electrophoresis, cellular DNA was prepared as described (Essmann et al., 2003). 24 hours after transfection, cells in 35 mm wells were lysed in 0.2 ml lysis buffer (20 mM Tris-HCl, 0.5 mM EDTA, pH 8.0) containing 0.25% NP-40 and 50 µg RNase A at 37° C. for 30 minutes. Each cell lysate was treated with 0.2 mg proteinase K for another 30 minutes at 37° C. and centrifuged at 10,000 g for 10 minutes at 25° C. Supernatant containing fragmented DNA was analyzed on 2% agarose gel. DNA fragmentation was also determined by flow cytometry after DNA staining with PI. 24 hours after transfection, cells were washed twice with cold PBS and subsequently resuspended in PBS containing 50 µg/ml PI and 20 µg/ml RNaseA. Cells were incubated at room temperature for ~30 minutes prior to analysis and were protected from light. DNA contents were analyzed using Coulter Cytomics FC500 Flow Cytometer (Coulter Electronics). Assessment of mitochondrial membrane potential and confocal microscopy Mitochondrial membrane potential was measured following the protocol of Pratt and Niu (Pratt and Niu, 2003). Transiently transfected HeLa cells were incubated for 2 hours in medium containing 50 nM MitoTracker Red (CM-H2 TMRos) (Molecular Probes), which develops fluorescence in cells with an intact mitochondrial membrane potential. Living cells were observed and photographed on a fluorescence microscope. MitoTracker-positive cells were counted from at least 200 GFP-positive cells. To observe intracellular localization of GFP fusion proteins, fixed HeLa cells were used for confocal microscopy. HeLa cells were transfected as described above on LabTek II chamber slides and cultured in the presence of 50 µM OPH. 18 hours after transfection, cells were stained with 50 nM MitoTracker Red (CM-H2 TMRos) and washed with PBS followed by fixation with 4% formaldehyde. Cells finally were washed, mounted and analyzed with a confocal microscope Zeiss LSM 510 (Carl Zeiss Microscopy, Jena, Germany) equipped with a 63x objective. Image acquisition was performed at room temperature.

Western Blotting

For western blotting, monoclonal anti-GFP antibody and anti-goat horseradish peroxidase (HRP) antibody were purchased from Santa Cruz Biotechnology. Anti- _-actin antibody was purchased from Sigma. The monoclonal anti-Flag 9E10.2 antibody was purchased from Invitrogen. The anti-mouse HRP antibody was purchased from Amersham Pharmacia. Monoclonal anti-cytochrome c 7H8.2C12 antibody, monoclonal anti-Bcl-xL 2H12 antibody, monoclonal anti-Bax 6A7 antibody, Polyclonal anti-Bak antibody were purchased from BD Biosciences, Sigma, Zymed Laboratory and from Upstate Biotechnology, respectively. For immunoblot analysis, 20 µg of protein was subjected to SDS-PAGE and transferred onto a PVDF membrane, which was blocked with 5% skimmed milk, probed with primary antibodies and visualized using an ECL chemiluminescence kit (Amersham Pharmacia).

Peptide Synthesis and Lipid Bilayer Experiment

The 29-mer ATAP peptide (KFEPKSGWMTFLEVTG-KICEMLSLLKQYC) (SEQ ID NO.: 36) corresponding to the C-terminus of Bfl1 and its mutant mHR7 (KFEP-KSGWMTFLQVTG-LICQMLSLLKQYC) (SEQ ID NO.: 50) were synthesized by Abgent (San Diego, Calif.) with 99% purity as measured by HPLC and mass spectrometry. The peptides were dissolved in DMSO to make a 10 mM stock. Phospholipids were purchased from Avanti Polar Lipids (Birmingham, Ala.). Electrophysiological analysis was performed as described (Lam et al., 1998; Ma et al., 1988). Lipid bilayer membranes were formed across an aperture of 200 µm diameter with a 1:1 mixture of bovine brain phosphatidylethanolamine and bovine brain phosphatidylserine dissolved in n-decane at a concentration of 25 mg/ml. The recording solutions contained: cis, 200 mM KCl and 10 mM HEPES-Tris (pH 7.4); trans, 50 mM NaCl, 10 mM HEPES-Tris (pH 7.4). 1 nl of 10 mM peptides dissolved in DMSO were added into 900 nl of cis solution and fused into the bilayer. Voltage manipulation and currents were measured using an Axopatch 200 A amplifier (Axon Instruments, Foster City, Calif.). Data analyses were preformed with pClamp and TIPS software.

Assay for Cytochrome c Release from Mitochondria

Mitochondria-free cytosol was prepared as previously described (Ko et al., 2003a). Briefly, 24 hours after transfection, HEK293 cells were collected by scraping, washed twice with ice-cold PBS, suspended in 100 nl extraction buffer (50 mM PIPES-KOH, pH 7.4, 200 mM mannitol, 70 mM sucrose, 50 mM KCl, 5 mM EGTA, 2 mM MgCl2, 1 mM dithiothreitol and protease inhibitors), and incubated on ice for 30 minutes. Cells were lysed by Dounce homogenization and homogenates were centrifuged at 100,000 g for 15 minutes at 4° C. Supernatants were harvested and 20 µg of protein was analyzed by western blotting using monoclonal anticytochrome c antibody. For in vitro analysis of cytochrome c release, heavy membranes enriched in mitochondria were isolated from BMK-D3 cells using a mitochondria fractionation kit (Active Motif) according to the instructions of the manufacturer. Isolated mitochondria were diluted to a concentration of 1 mg/ml in the extraction buffer and incubated with synthetic ATAP or mHR7 peptides (100 µM) or DMSO as control for 1 hour at 37° C. The reactions were then centrifuged at 13,000 g for 10 minutes and the resulting pellets and supernatants were analyzed by SDS-PAGE.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. An isolated polypeptide comprising SEQ ID NO:36, an analog or derivative thereof, wherein the polypeptide, analog, or derivative thereof forms pores in the mitochondrial outer membrane, wherein the polypeptide, analog, or derivative thereof is 29 to 60 amino acids long.

2. An isolated polypeptide, wherein the polypeptide is a member selected from the group consisting of SEQ ID NO. 36, 38, 39, 40, 41, 42, 43, 44, 45, 46, 47, 48, 49, 50, and 51.

3. A fusion protein comprising:
a first polypeptide including the amino acid sequence of general formula (I):

$$bXaXbuunnunnanXGbnXannXnn(X)_{0-2}bXYC \quad (I)$$

wherein,
n=a nonpolar (hydrophobic) amino acid;
X=any amino acid;
u=a polar, uncharged amino acid;
b=a basic amino acid;
a=an acidic amino acid; and wherein the first polypeptide forms pores in the mitochondrial outer membrane; and
at least one additional heterologous peptide disposed at any one of the amino terminus, the carboxy terminus, or both, and wherein the first polypeptide and the additional heterologous peptide are disposed in a single, contiguous polypeptide chain of 31 to 60 amino acids long.

4. The fusion protein of claim 3, wherein the at least one additional polypeptide comprises a TAT polypeptide or portion thereof.

5. The fusion protein of claim 4, wherein the fusion protein further comprises a HIS tag.

6. A therapeutic composition comprising a pharmaceutically acceptable excipient or carrier, and an effective amount of a polypeptide comprising the amino acid sequence of general formula (I):

$$bXaXbuunnunnanXGbnXannXnn(X)_{0-2}bXYC \quad (I)$$

wherein,
n=a nonpolar (hydrophobic) amino acid;
X=any amino acid;
u=a polar, uncharged amino acid;
b=a basic amino acid;
a=an acidic amino acid; and
the polypeptide forms pores in the mitochondrial outer membrane and 29 to 60 amino acids long.

7. The therapeutic composition of claim 6, wherein the polypeptide is at least one member selected from the group consisting of SEQ ID NO. 36, 38, 39, 40, 41, 42, 43, 44, 45, 46, 47, 48, 49, and 50.

8. An isolated polypeptide comprising the general formula (II):

$$(K/R)n(E/D)(P)(K/R)(S/T)GW(M/L)(S/T)FL(E/D)nTG(K/R)(I/V/L)(X)(E/D)ML(X)_{1-6}LL(X)_{0-2}(K/R)XYC \quad (II)$$

wherein,
n=a nonpolar (hydrophobic) amino acid; and
X=any amino acid, wherein the polypeptide forms pores in the mitochondrial outer membrane and is 29 to 60 amino acids long.

9. A method of treating a bacterial infection comprising administering to a subject an effective amount of composition comprising the composition of claim 6, together with a pharmaceutically acceptable carrier.

10. A composition comprising a pharmaceutically acceptable carrier and an effective amount of a peptide with the sequence as set forth in SEQ ID NO.: 36 and is 29 to 60 amino acids long.

11. An isolated polypeptide comprising the amino acid sequence of general formula:

$$(K/R)X(E/D)X(K/R)uunnunn(E/D)nXG(K/R)nX(E/D)nnXnn(K/R)_{1-2}(X)_{1-4}C$$

wherein,
   n=a nonpolar (hydrophobic) amino acid;
   X=any amino acid,
   u=a polar, uncharged amino acid; and
   the polypeptide forms pores in the mitochondrial outer membrane and is 29 to 60 amino acids long.

12. A composition comprising a pharmaceutically acceptable carrier and an effective amount of the polypeptide of claim 11.

* * * * *

```
                        SEQUENCE LISTING

<160> NUMBER OF SEQ ID NOS: 65

<210> SEQ ID NO 1
<211> LENGTH: 528
<212> TYPE: DNA
<213> ORGANISM: Homo sapiens
<220> FEATURE:
<221> NAME/KEY: misc_feature
<222> LOCATION: (1)..(528)
<223> OTHER INFORMATION: Human Bfl-1 cDNA

<400> SEQUENCE: 1
atgacagact gtgaatttgg atatatttac aggctggctc aggactatct gcagtgcgtc      60
ctacagatac cacaacctgg atcaggtcca agcaaaacgt ccagagtgct acaaaatgtt    120
gcgttctcag tccaaaaaga agtggaaaag aatctgaagt catgcttgga caatgttaat    180
gttgtgtccg tagacactgc cagaacacta ttcaaccaag tgatggaaaa ggagtttgaa    240
gacggcatca ttaactgggg aagaattgta accatatttg catttgaagg tattctcatc    300
aagaaacttc tacgacagca aattgccccg gatgtggata cctataagga gatttcatat    360
tttgttgcgg agttcataat gaataacaca ggagaatgga taaggcaaaa cggaggctgg    420
gaaaatggct ttgtaaagaa gtttgaacct aaatctggct ggatgacttt tctagaagtt    480
acaggaaaga tctgtgaaat gctatctctc ctgaagcaat actgttga                528

<210> SEQ ID NO 2
<211> LENGTH: 175
<212> TYPE: PRT
<213> ORGANISM: Homo sapiens
<220> FEATURE:
<221> NAME/KEY: MISC_FEATURE
<222> LOCATION: (1)..(175)
<223> OTHER INFORMATION: Human Bfl-1 protein

<400> SEQUENCE: 2

Met Thr Asp Cys Glu Phe Gly Tyr Ile Tyr Arg Leu Ala Gln Asp Tyr
1               5                   10                  15

Leu Gln Cys Val Leu Gln Ile Pro Gln Pro Gly Ser Gly Pro Ser Lys
                20                  25                  30

Thr Ser Arg Val Leu Gln Asn Val Ala Phe Ser Val Gln Lys Glu Val
            35                  40                  45

Glu Lys Asn Leu Lys Ser Cys Leu Asp Asn Val Asn Val Val Ser Val
        50                  55                  60

Asp Thr Ala Arg Thr Leu Phe Asn Gln Val Met Glu Lys Glu Phe Glu
65                  70                  75                  80

Asp Gly Ile Ile Asn Trp Gly Arg Ile Val Thr Ile Phe Ala Phe Glu
                85                  90                  95

Gly Ile Leu Ile Lys Lys Leu Leu Arg Gln Gln Ile Ala Pro Asp Val
```

```
                100              105                  110
Asp Thr Tyr Lys Glu Ile Ser Tyr Phe Val Ala Glu Phe Ile Met Asn
            115                 120                 125

Asn Thr Gly Glu Trp Ile Arg Gln Asn Gly Gly Trp Glu Asn Gly Phe
        130                 135                 140

Val Lys Lys Phe Glu Pro Lys Ser Gly Trp Met Thr Phe Leu Glu Val
145                 150                 155                 160

Thr Gly Lys Ile Cys Glu Met Leu Ser Leu Leu Lys Gln Tyr Cys
                165                 170                 175

<210> SEQ ID NO 3
<211> LENGTH: 172
<212> TYPE: PRT
<213> ORGANISM: Mus musculus
<220> FEATURE:
<221> NAME/KEY: MISC_FEATURE
<222> LOCATION: (1)..(172)
<223> OTHER INFORMATION: Mouse Bfl-1 (Bcl-2-related protein A1 )

<400> SEQUENCE: 3

Met Ala Glu Ser Glu Leu Met His Ile His Ser Leu Ala Glu His Tyr
1               5                   10                  15

Leu Gln Tyr Val Leu Gln Val Pro Ala Phe Glu Ser Ala Pro Ser Gln
            20                  25                  30

Ala Cys Arg Val Leu Gln Arg Val Ala Phe Ser Val Gln Lys Glu Val
        35                  40                  45

Glu Lys Asn Leu Lys Ser Tyr Leu Asp Asp Phe His Val Glu Ser Ile
    50                  55                  60

Asp Thr Ala Arg Ile Ile Phe Asn Gln Val Met Glu Lys Glu Phe Glu
65                  70                  75                  80

Asp Gly Ile Ile Asn Trp Gly Arg Ile Val Thr Ile Phe Ala Phe Gly
                85                  90                  95

Gly Val Leu Leu Lys Lys Leu Pro Gln Glu Gln Ile Ala Leu Asp Val
            100                 105                 110

Cys Ala Tyr Lys Gln Val Ser Ser Phe Val Ala Glu Phe Ile Met Asn
        115                 120                 125

Asn Thr Gly Glu Trp Ile Arg Gln Asn Gly Gly Trp Glu Asp Gly Phe
    130                 135                 140

Ile Lys Lys Phe Glu Pro Lys Ser Gly Trp Leu Thr Phe Leu Gln Met
145                 150                 155                 160

Thr Gly Gln Ile Trp Glu Met Leu Phe Leu Leu Lys
                165                 170

<210> SEQ ID NO 4
<211> LENGTH: 239
<212> TYPE: PRT
<213> ORGANISM: Homo sapiens
<220> FEATURE:
<221> NAME/KEY: MISC_FEATURE
<222> LOCATION: (1)..(239)
<223> OTHER INFORMATION: Human Bcl-2 protein

<400> SEQUENCE: 4

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Gly Ala Ala Pro Ala Pro Gly Ile
        35                  40                  45
```

```
Phe Ser Ser Gln Pro Gly His Thr Pro His Pro Ala Ala Ser Arg Asp
            50                  55                  60
Pro Val Ala Arg Thr Ser Pro Leu Gln Thr Pro Ala Ala Pro Gly Ala
 65                  70                  75                  80
Ala Ala Gly Pro Ala Leu Ser Pro Val Pro Val Val His Leu Thr
                85                  90                  95
Leu Arg Gln Ala Gly Asp Asp Phe Ser Arg Arg Tyr Arg Arg Asp Phe
                100                 105                 110
Ala Glu Met Ser Ser Gln Leu His Leu Thr Pro Phe Thr Ala Arg Gly
            115                 120                 125
Arg Phe Ala Thr Val Val Glu Glu Leu Phe Arg Asp Gly Val Asn Trp
    130                 135                 140
Gly Arg Ile Val Ala Phe Phe Glu Phe Gly Gly Val Met Cys Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Asp Ala Phe Val Glu Leu Tyr Gly Pro Ser Met Arg Pro
        195                 200                 205
Leu Phe Asp Phe Ser Trp Leu Ser Leu Lys Thr Leu Leu Ser Leu Ala
    210                 215                 220
Leu Val Gly Ala Cys Ile Thr Leu Gly Ala Tyr Leu Gly His Lys
225                 230                 235

<210> SEQ ID NO 5
<211> LENGTH: 233
<212> TYPE: PRT
<213> ORGANISM: Homo sapiens
<220> FEATURE:
<221> NAME/KEY: MISC_FEATURE
<222> LOCATION: (1)..(233)
<223> OTHER INFORMATION: Human Bcl-xL

<400> SEQUENCE: 5

Met Ser Gln Ser Asn Arg Glu Leu Val Val Asp Phe Leu Ser Tyr Lys
 1               5                  10                  15
Leu Ser Gln Lys Gly Tyr Ser Trp Ser Gln Phe Ser Asp Val Glu Glu
            20                  25                  30
Asn Arg Thr Glu Ala Pro Glu Gly Thr Glu Ser Glu Met Glu Thr Pro
        35                  40                  45
Ser Ala Ile Asn Gly Asn Pro Ser Trp His Leu Ala Asp Ser Pro Ala
    50                  55                  60
Val Asn Gly Ala Thr Ala His Ser Ser Ser Leu Asp Ala Arg Glu Val
 65                  70                  75                  80
Ile Pro Met Ala Ala Val Lys Gln Ala Leu Arg Glu Ala Gly Asp Glu
                85                  90                  95
Phe Glu Leu Arg Tyr Arg Arg Ala Phe Ser Asp Leu Thr Ser Gln Leu
                100                 105                 110
His Ile Thr Pro Gly Thr Ala Tyr Gln Ser Phe Glu Gln Val Val Asn
            115                 120                 125
Glu Leu Phe Arg Asp Gly Val Asn Trp Gly Arg Ile Val Ala Phe Phe
        130                 135                 140
Ser Phe Gly Gly Ala Leu Cys Val Glu Ser Val Asp Lys Glu Met Gln
145                 150                 155                 160
```

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
210                 215                 220

Leu Leu Gly Ser Leu Phe Ser Arg Lys
225                 230

<210> SEQ ID NO 6
<211> LENGTH: 193
<212> TYPE: PRT
<213> ORGANISM: Homo sapiens
<220> FEATURE:
<221> NAME/KEY: MISC_FEATURE
<222> LOCATION: (1)..(193)
<223> OTHER INFORMATION: Human Bcl-w

<400> SEQUENCE: 6

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 7
<211> LENGTH: 350
<212> TYPE: PRT
<213> ORGANISM: Homo sapiens
<220> FEATURE:
<221> NAME/KEY: MISC_FEATURE
<222> LOCATION: (1)..(350)
<223> OTHER INFORMATION: Human Mcl-1

<400> SEQUENCE: 7

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Asp Asp Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 8
<211> LENGTH: 33
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(33)
<223> OTHER INFORMATION: Primer(sense)

<400> SEQUENCE: 8
gcgaattcaa tgacagactg tgaatttgga tat                            33

<210> SEQ ID NO 9
<211> LENGTH: 36
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(36)
<223> OTHER INFORMATION: Primer(antisense)

<400> SEQUENCE: 9
aaggatcctc aacagtattg cttcaggaga gatagc                                 36

<210> SEQ ID NO 10
<211> LENGTH: 34
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(34)
<223> OTHER INFORMATION: Primer

<400> SEQUENCE: 10
aactcgagct aagtttgaac ctaaatctgg ctgg                                   34

<210> SEQ ID NO 11
<211> LENGTH: 33
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(33)
<223> OTHER INFORMATION: Primer

<400> SEQUENCE: 11
ttgaattcaa cagtattgct tcaggagaga tag                                    33

<210> SEQ ID NO 12
<211> LENGTH: 34
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(34)
<223> OTHER INFORMATION: Primer

<400> SEQUENCE: 12
aactcgagct ctgtttgaac ctaaatctgg ctgg                                   34

<210> SEQ ID NO 13
<211> LENGTH: 43
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(43)
<223> OTHER INFORMATION: Primer

<400> SEQUENCE: 13
aactcgagct aagtttgaac ctctatctgg ctggatgact ttt         43

<210> SEQ ID NO 14
<211> LENGTH: 43
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(43)
<223> OTHER INFORMATION: Primer

<400> SEQUENCE: 14
aactcgagct ctgtttgaac ctctatctgg ctggatgact ttt         43

<210> SEQ ID NO 15
<211> LENGTH: 41
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(41)
<223> OTHER INFORMATION: Primer

<400> SEQUENCE: 15
ttgaattcaa cagtattgca gcaggagaga tagcatttca c           41

<210> SEQ ID NO 16
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

<400> SEQUENCE: 16
aactcgagct aagtttgaac ctaaatctgg ctggatgact tttctagaag ttacaggaaa    60
gatctgt                                                              67

<210> SEQ ID NO 17
<211> LENGTH: 59
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 17
ttgaattcaa cagtattgct tcaggagaga tagcatttca cagatctttc ctgtaactt     59

<210> SEQ ID NO 18
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

```
<400> SEQUENCE: 18
aactcgagct aagtttgaac ctaaatctgg ctggatgact tttctacaag ttacaggaaa      60
gatctgt                                                                67

<210> SEQ ID NO 19
<211> LENGTH: 59
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 19
ttgaattcaa cagtattgct tcaggagaga tagcatttga cagatctttc ctgtaactt      59

<210> SEQ ID NO 20
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

<400> SEQUENCE: 20
aactcgagct aagtttgaac ctaaatctgg ctggatgact tttctactag ttacaggaaa      60
gatctgt                                                                67

<210> SEQ ID NO 21
<211> LENGTH: 59
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 21
ttgaattcaa cagtattgct tcaggagaga tagcattaga cagatctttc ctgtaactt      59

<210> SEQ ID NO 22
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

<400> SEQUENCE: 22
aactcgagct aagtttgaac ctaaatctgg ctggatgact tttctaaagg ttacaggaaa      60
gatctgt                                                                67

<210> SEQ ID NO 23
<211> LENGTH: 59
<212> TYPE: DNA
```

```
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 23
ttgaattcaa cagtattgct tcaggagaga tagcatctta cagatctttc ctgtaactt      59

<210> SEQ ID NO 24
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

<400> SEQUENCE: 24
aactcgagct aagtttgaac ctaaatctgg ctggatgact tttctagaag ttacaggact      60
aatctgt                                                                67

<210> SEQ ID NO 25
<211> LENGTH: 59
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 25
ttgaattcaa cagtattgct tcaggagaga tagcatttca cagattagtc ctgtaactt      59

<210> SEQ ID NO 26
<211> LENGTH: 67
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(67)
<223> OTHER INFORMATION: Primer

<400> SEQUENCE: 26
aactcgagct aagtttgaac ctaaatctgg ctggatgact tttctacaag ttacaggact      60
aatctgt                                                                67

<210> SEQ ID NO 27
<211> LENGTH: 59
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(59)
<223> OTHER INFORMATION: Primer

<400> SEQUENCE: 27
ttgaattcaa cagtattgct tcaggagaga tagcatttga cagattagtc ctgtaactt      59
```

<210> SEQ ID NO 28
<211> LENGTH: 79
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(79)
<223> OTHER INFORMATION: Primer

<400> SEQUENCE: 28
aactcgagct gagagccgaa agggccagga acgcttcaac cgctggttcc tgacgggcat     60
gactgtggcc ggcgtggtt                                                  79

<210> SEQ ID NO 29
<211> LENGTH: 54
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(54)
<223> OTHER INFORMATION: Primer

<400> SEQUENCE: 29
ttgaattcat ttccgactga agagtgagcc cagcagaacc acgccggcca cagt            54

<210> SEQ ID NO 30
<211> LENGTH: 69
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(69)
<223> OTHER INFORMATION: Primer

<400> SEQUENCE: 30
tcgaggctgg atgactttc tagaagttac aggaaagatc tgtgaaatgc tatctctcct      60
gaagcaatg                                                             69

<210> SEQ ID NO 31
<211> LENGTH: 69
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(69)
<223> OTHER INFORMATION: Primer

<400> SEQUENCE: 31
aattcattgc ttcaggagag atagcatttc acagatcttt cctgtaactt ctagaaaagt     60
catccagcc                                                             69

<210> SEQ ID NO 32
<211> LENGTH: 43
<212> TYPE: DNA
<213> ORGANISM: Artificial
<220> FEATURE:
<223> OTHER INFORMATION: Artificial Sequence
<220> FEATURE:

```
<221> NAME/KEY: misc_feature
<222> LOCATION: (1)..(43)
<223> OTHER INFORMATION: Primer

<400> SEQUENCE: 32
ccggactccc cgcccagatc accttcctga gcgtgcccgg ctc          43

<210> SEQ ID NO 33
<211> LENGTH: 43
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(43)
<223> OTHER INFORMATION: Primer

<400> SEQUENCE: 33
tcgagagccg ggcacgctca ggaaggtgat ctgggcgggg agt          43

<210> SEQ ID NO 34
<211> LENGTH: 75
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(75)
<223> OTHER INFORMATION: Primer

<400> SEQUENCE: 34
ccgctagcgc taccggtcgc caccatggac tacaaagacg atgacgacaa gcttgaattc  60
gattttccac ctccc                                                  75

<210> SEQ ID NO 35
<211> LENGTH: 74
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(74)
<223> OTHER INFORMATION: Primer

<400> SEQUENCE: 35
agctcgagat ctgagtccgg acttgtagct gcccagttct tcatcggtag ggggaggtgg  60
aaaatcgaat tcaa                                                   74

<210> SEQ ID NO 36
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: ATAP peptide derived from residues 147-175 of
      Bfl-1

<400> SEQUENCE: 36

Lys Phe Glu Pro Lys Ser Gly Trp Met Thr Phe Leu Glu Val Thr Gly
1               5                   10                  15

Lys Ile Cys Glu Met Leu Ser Leu Leu Lys Gln Tyr Cys
            20                  25
```

<210> SEQ ID NO 37
<211> LENGTH: 87
<212> TYPE: DNA
<213> ORGANISM: Homo sapiens
<220> FEATURE:
<221> NAME/KEY: misc_feature
<222> LOCATION: (1)..(87)
<223> OTHER INFORMATION: ATAP cDNA (derived from Bfl-1)

<400> SEQUENCE: 37
aagtttgaac ctaaatctgg ctggatgact tttctagaag ttacaggaaa gatctgtgaa     60
atgctatctc tcctgaagca atactgt                                        87

<210> SEQ ID NO 38
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K147L - ATAP

<400> SEQUENCE: 38

Leu Phe Glu Pro Lys Ser Gly Trp Met Thr Phe Leu Glu Val Thr Gly
1               5                   10                  15

Lys Ile Cys Glu Met Leu Ser Leu Leu Lys Gln Tyr Cys
            20                  25

<210> SEQ ID NO 39
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K151L - ATAP

<400> SEQUENCE: 39

Lys Phe Glu Pro Leu Ser Gly Trp Met Thr Phe Leu Glu Val Thr Gly
1               5                   10                  15

Lys Ile Cys Glu Met Leu Ser Leu Leu Lys Gln Tyr Cys
            20                  25

<210> SEQ ID NO 40
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K172L - ATAP

<400> SEQUENCE: 40

Lys Phe Glu Pro Lys Ser Gly Trp Met Thr Phe Leu Glu Val Thr Gly
1               5                   10                  15

Lys Ile Cys Glu Met Leu Ser Leu Leu Leu Gln Tyr Cys
            20                  25

<210> SEQ ID NO 41
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K147L, K151L - ATAP

```
<400> SEQUENCE: 41

Leu Phe Glu Pro Leu Ser Gly Trp Met Thr Phe Leu Glu Val Thr Gly
1               5                   10                  15

Lys Ile Cys Glu Met Leu Ser Leu Leu Lys Gln Tyr Cys
            20                  25

<210> SEQ ID NO 42
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K147L, K172L - ATAP

<400> SEQUENCE: 42

Leu Phe Glu Pro Lys Ser Gly Trp Met Thr Phe Leu Glu Val Thr Gly
1               5                   10                  15

Lys Ile Cys Glu Met Leu Ser Leu Leu Leu Gln Tyr Cys
            20                  25

<210> SEQ ID NO 43
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K151L, K172L - ATAP

<400> SEQUENCE: 43

Lys Phe Glu Pro Leu Ser Gly Trp Met Thr Phe Leu Glu Val Thr Gly
1               5                   10                  15

Lys Ile Cys Glu Met Leu Ser Leu Leu Leu Gln Tyr Cys
            20                  25

<210> SEQ ID NO 44
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: K147L, K151L, K172L - ATAP

<400> SEQUENCE: 44

Leu Phe Glu Pro Leu Ser Gly Trp Met Thr Phe Leu Glu Val Thr Gly
1               5                   10                  15

Lys Ile Cys Glu Met Leu Ser Leu Leu Leu Gln Tyr Cys
            20                  25

<210> SEQ ID NO 45
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E159Q - ATAP

<400> SEQUENCE: 45

Lys Phe Glu Pro Lys Ser Gly Trp Met Thr Phe Leu Gln Val Thr Gly
1               5                   10                  15

Lys Ile Cys Glu Met Leu Ser Leu Leu Lys Gln Tyr Cys
```

20                  25

<210> SEQ ID NO 46
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E166Q - ATAP

<400> SEQUENCE: 46

Lys Phe Glu Pro Lys Ser Gly Trp Met Thr Phe Leu Glu Val Thr Gly
1               5                   10                  15

Lys Ile Cys Gln Met Leu Ser Leu Leu Lys Gln Tyr Cys
            20                  25

<210> SEQ ID NO 47
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E159Q, E166Q - ATAP

<400> SEQUENCE: 47

Lys Phe Glu Pro Lys Ser Gly Trp Met Thr Phe Leu Gln Val Thr Gly
1               5                   10                  15

Lys Ile Cys Gln Met Leu Ser Leu Leu Lys Gln Tyr Cys
            20                  25

<210> SEQ ID NO 48
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E159L, E166L - ATAP

<400> SEQUENCE: 48

Lys Phe Glu Pro Lys Ser Gly Trp Met Thr Phe Leu Leu Val Thr Gly
1               5                   10                  15

Lys Ile Cys Leu Met Leu Ser Leu Leu Lys Gln Tyr Cys
            20                  25

<210> SEQ ID NO 49
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E159K, E166K - ATAP

<400> SEQUENCE: 49

Lys Phe Glu Pro Lys Ser Gly Trp Met Thr Phe Leu Lys Val Thr Gly
1               5                   10                  15

Lys Ile Cys Lys Met Leu Ser Leu Leu Lys Gln Tyr Cys
            20                  25

<210> SEQ ID NO 50
<211> LENGTH: 29
<212> TYPE: PRT
<213> ORGANISM: Homo sapiens -continued

```
<220> FEATURE:
<221> NAME/KEY: MISC_FEATURE
<222> LOCATION: (1)..(29)
<223> OTHER INFORMATION: K163L - ATAP

<400> SEQUENCE: 50

Lys Phe Glu Pro Lys Ser Gly Trp Met Thr Phe Leu Glu Val Thr Gly
1               5                   10                  15

Leu Ile Cys Glu Met Leu Ser Leu Leu Lys Gln Tyr Cys
            20                  25

<210> SEQ ID NO 51
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: E159Q, K163L, E166Q - ATAP

<400> SEQUENCE: 51

Lys Phe Glu Pro Lys Ser Gly Trp Met Thr Phe Leu Gln Val Thr Gly
1               5                   10                  15

Leu Ile Cys Gln Met Leu Ser Leu Leu Lys Gln Tyr Cys
            20                  25

<210> SEQ ID NO 52
<211> LENGTH: 91
<212> TYPE: PRT
<213> ORGANISM: Homo sapiens
<220> FEATURE:
<221> NAME/KEY: MISC_FEATURE
<222> LOCATION: (1)..(85)
<223> OTHER INFORMATION: Human HCCS-1 protein

<400> SEQUENCE: 52

Met Arg Val Ser Phe Cys Arg Pro Gly Trp Ser Ala Met Ala Arg Ser
1               5                   10                  15

Arg Leu Thr Ala Thr Ser Val Ser Gln Val Gln Glu Asn Gly Phe Val
            20                  25                  30

Lys Lys Leu Glu Pro Lys Ser Gly Trp Met Thr Phe Leu Glu Val Thr
        35                  40                  45

Gly Lys Ile Cys Glu Met Leu Phe Cys Pro Glu Ala Ile Leu Leu Thr
    50                  55                  60

Arg Lys Asp Thr Pro Tyr Cys Glu Thr Gly Leu Ile Phe Leu Thr Leu
65                  70                  75                  80

Thr Lys Thr Ile Ala Asn Thr Tyr Phe Tyr Phe
                85                  90

<210> SEQ ID NO 53
<211> LENGTH: 38
<212> TYPE: PRT
<213> ORGANISM: Homo sapiens
<220> FEATURE:
<221> NAME/KEY: MISC_FEATURE
<222> LOCATION: (1)..(42)
<223> OTHER INFORMATION: ATAP peptide from human HCCS-1

<400> SEQUENCE: 53

Lys Leu Glu Pro Lys Ser Gly Trp Met Thr Phe Leu Glu Val Thr Gly
1               5                   10                  15

Lys Ile Cys Glu Met Leu Phe Cys Pro Glu Ala Ile Leu Leu Thr Arg
            20                  25                  30
```

Lys Asp Thr Pro Tyr Cys
         35

<210> SEQ ID NO 54
<211> LENGTH: 240
<212> TYPE: DNA
<213> ORGANISM: Homo sapiens
<220> FEATURE:
<221> NAME/KEY: misc_feature
<222> LOCATION: (1)..(240)
<223> OTHER INFORMATION: HCCS-1 human, cDNA from Met 13 to stop

<400> SEQUENCE: 54
atggcgcgat ctcggctcac tgcaacctct gtctcccagg ttcaggaaaa tggctttgta      60
aagaagcttg agcctaaatc tggctggatg acttttctag aagttacagg aaagatctgt     120
gaaatgctct tctgtcctga agcaatactg ttgaccagaa aggacactct atattgtgaa     180
accggcctaa tttttctgac tcttacgaaa acgattgcca acacatactt ctacttttaa     240

<210> SEQ ID NO 55
<211> LENGTH: 49
<212> TYPE: DNA
<213> ORGANISM: Artificial
<220> FEATURE:
<223> OTHER INFORMATION: Artifical Sequence
<220> FEATURE:
<221> NAME/KEY: misc_feature
<222> LOCATION: (1)..(49)
<223> OTHER INFORMATION: Artificial Sequence

<400> SEQUENCE: 55
aacgtctcaa ggaaagatct gtcagatgct cttctgtcct gaagcaata                 49

<210> SEQ ID NO 56
<211> LENGTH: 46
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(46)
<223> OTHER INFORMATION: Artificial Sequence

<400> SEQUENCE: 56
aacgtctcat cctgtaacct gtagaaaagt catccagcca gattta                    46

<210> SEQ ID NO 57
<211> LENGTH: 34
<212> TYPE: DNA
<213> ORGANISM: Artificial
<220> FEATURE:
<223> OTHER INFORMATION: Artificial Sequence
<220> FEATURE:
<221> NAME/KEY: misc_feature
<222> LOCATION: (1)..(34)
<223> OTHER INFORMATION: Artificial Sequence

<400> SEQUENCE: 57
aatccggaat gagagtttca ttctgtcgcc cagg                                 34

<210> SEQ ID NO 58
<211> LENGTH: 35
<212> TYPE: DNA
<213> ORGANISM: Artificial
<220> FEATURE:
<223> OTHER INFORMATION: Artificial Sequence
<220> FEATURE:

```
<221> NAME/KEY: misc_feature
<222> LOCATION: (1)..(35)
<223> OTHER INFORMATION: Artificial Sequence

<400> SEQUENCE: 58
aagaattcaa aagtagaagt atgtgttggc aatcg                              35

<210> SEQ ID NO 59
<211> LENGTH: 117
<212> TYPE: DNA
<213> ORGANISM: Homo sapiens
<220> FEATURE:
<221> NAME/KEY: misc_feature
<222> LOCATION: (1)..(117)
<223> OTHER INFORMATION: Human HCCS-1 ATAP nucleic acid

<400> SEQUENCE: 59
aagcttgagc ctaaatctgg ctggatgact tttctagaag ttacaggaaa gatctgtgaa    60
atgctcttct gtcctgaagc aatactgttg accagaaagg acactctata ttgtgaa     117

<210> SEQ ID NO 60
<211> LENGTH: 24
<212> TYPE: DNA
<213> ORGANISM: Artificial Sequence
<220> FEATURE:
<223> OTHER INFORMATION: Sythetic nucleic acid sequence
<220> FEATURE:
<221> NAME/KEY: misc_feature
<222> LOCATION: (1)..(24)

<400> SEQUENCE: 60
acaaaatgtt gcgttctcag tcca                                          24

<210> SEQ ID NO 61
<211> LENGTH: 22
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(22)

<400> SEQUENCE: 61
cgttttgcct tatccattct cc                                            22

<210> SEQ ID NO 62
<211> LENGTH: 22
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(22)

<400> SEQUENCE: 62
ttgccacaaa tggtgtgctc ta                                            22

<210> SEQ ID NO 63
<211> LENGTH: 22
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(22)
```

-continued

```
<400> SEQUENCE: 63
tcctggtgcc atgatttact gt                                              22

<210> SEQ ID NO 64
<211> LENGTH: 22
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(22)

<400> SEQUENCE: 64
gatcagcaag caggagtatg ac                                              22

<210> SEQ ID NO 65
<211> LENGTH: 22
<212> TYPE: DNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(22)

<400> SEQUENCE: 65
atggcaaggg acttcctgta ac                                              22
```